(12) United States Patent  (10) Patent No.: US 8,124,567 B2
Walter et al.  (45) Date of Patent: Feb. 28, 2012

(54) FUNGICIDAL COMPOSITIONS

(75) Inventors: Harald Walter, Basel (CH); Camilla Corsi, Basel (CH); Josef Ehrenfreund, Basel (CH); Clemens Lamberth, Basel (CH); Hans Tobler, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 730 days.

(21) Appl. No.: 11/696,908

(22) Filed: Apr. 5, 2007

(65) Prior Publication Data

US 2007/0265267 A1 Nov. 15, 2007

Related U.S. Application Data

(63) Continuation-in-part of application No. 11/576,719, filed as application No. PCT/EP2005/010755 on Oct. 6, 2005.

(30) Foreign Application Priority Data

Oct. 8, 2004 (GB) .................................. 0422401.0

(51) Int. Cl.
*A01N 43/64* (2006.01)
*A01N 43/00* (2006.01)
(52) U.S. Cl. ........................................ 504/134; 504/139
(58) Field of Classification Search .................. 504/129
See application file for complete search history.

(56) References Cited

U.S. PATENT DOCUMENTS 6,444,692 B1 * 9/2002 Schelberger et al. ......... 514/384
2008/0051446 A1 * 2/2008 Ehrenfreund et al. ........ 514/406

FOREIGN PATENT DOCUMENTS

WO 2004/035589 A 4/2004
* cited by examiner

*Primary Examiner* — Alton Pryor
(74) *Attorney, Agent, or Firm* — R. Kody Jones

(57) ABSTRACT

A method of controlling phytopathogenic diseases on useful plants or on propagation material thereof, which comprises applying to the useful plants, the locus thereof or propagation material thereof a combination of components A) and B) in a synergistically effective amount, wherein
component A) is a compound of formula I

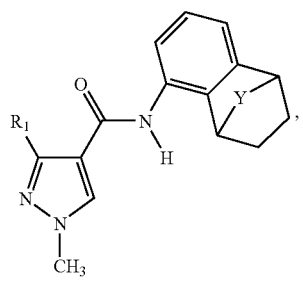

(I)

wherein $R_1$ is difluoromethyl or trifluoromethyl; Y is —$CHR_2$— or

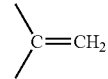

and $R_2$ is hydrogen or $C_1$-$C_6$alkyl; or a tautomer of such a compound; and
component B) is a compound selected from compounds known for their fungicidal and/or insecticidal activity, is particularly effective in controlling or preventing fungal diseases of useful plants.

14 Claims, No Drawings

FUNGICIDAL COMPOSITIONS

This application is a Continuation in Part of application Ser. No. 11/576,719 filed Apr. 5, 2007, still pending, which is the National Stage of International Application No. PCT/EP2005/010755 filed Oct. 6, 2005, which claims priority to GB 0422401.0 filed Oct. 8, 2004, the contents of which are incorporated herein by reference.

The present invention relates to novel fungicidal compositions for the treatment of phytopathogenic diseases of useful plants, especially phytopathogenic fungi, and to a method of controlling phytopathogenic diseases on useful plants.

It is known from WO 04/35589 that certain tricyclic carboxamide derivatives have biological activity against phytopathogenic fungi. On the other hand various fungicidal compounds of different chemical classes are widely known as plant fungicides for application in various crops of cultivated plants. However, crop tolerance and activity against phytopathogenic plant fungi do not always satisfy the needs of agricultural practice in many incidents and aspects.

There is therefore proposed in accordance with the present invention a method of controlling phytopathogenic diseases on useful plants or on propagation material thereof, which comprises applying to the useful plants, the locus thereof or propagation material thereof a combination of components A) and B) in a synergistically effective amount, wherein component A) is a compound of formula I

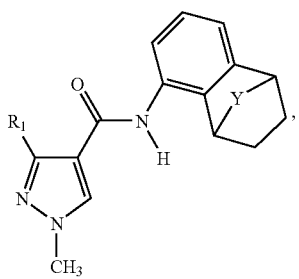

(I)

wherein
$R_1$ is difluoromethyl or trifluoromethyl; Y is —$CHR_2$— or

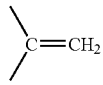

and $R_2$ is hydrogen or $C_1$-$C_6$alkyl; or a tautomer of such a compound; and component B) is a compound selected from the group consisting of
a strobilurin fungicide, such as azoxystrobin (47), dimoxystrobin (226), fluoxastrobin (382), kresoxim-methyl (485), metominostrobin (551), orysastrobin, picoxystrobin (647), pyraclostrobin (690), trifloxystrobin (832); and a compound of formula B-6

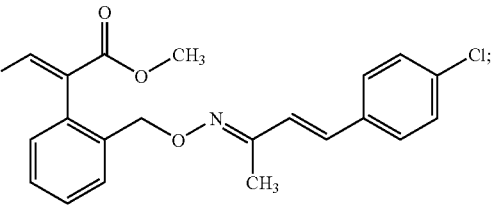

(B-6)

an azole fungicide, such as azaconazole (40), bromuconazole (96), cyproconazole (207), difenoconazole (247), diniconazole (267), diniconazole-M (267), epoxiconazole (298), fenbuconazole (329), fluquinconazole (386), flusilazole (393), flutriafol (397), hexaconazole (435), imazalil (449), imibenconazole (457), ipconazole (468), metconazole (525), myclobutanil (564), oxpoconazole (607), pefurazoate (618), penconazole (619), prochloraz (659), propiconazole (675), prothioconazole (685), simeconazole (731), tebuconazole (761), tetraconazole (778), triadimefon (814), triadimenol (815), triflumizole (834), triticonazole (842), diclobutrazol (1068), etaconazole (1129), furconazole (1198), furconazole-cis (1199) and quinconazole (1378);
a phenyl pyrrole fungicide, such as fenpiclonil (341) and fludioxonil (368);
an anilino-pyrimidine fungicide, such as cyprodinil (208), mepanipyrim (508) and pyrimethanil (705);
a morpholine fungicide, such as aldimorph, dodemorph (288), fenpropimorph (344), tridemorph (830), fenpropidin (343), spiroxamine (740); piperalin (648) and a compound of formula B-7

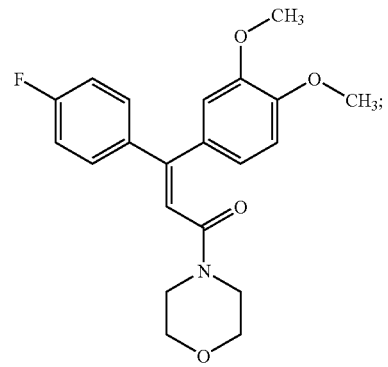

(B-7)

a compound of formula F-1

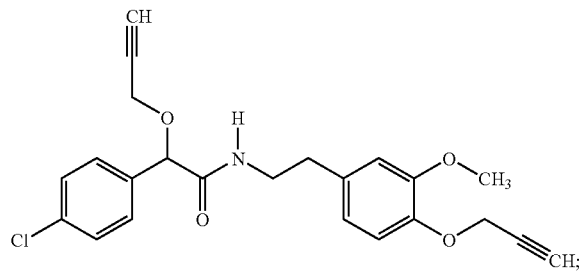

(F-1)

a compound of formula B-1

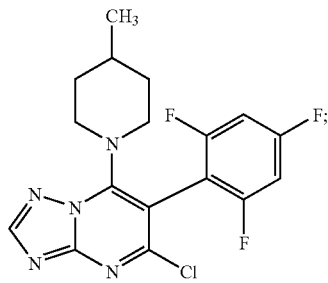
(B-1)

chlorothalonil (142); famoxadone (322); fenamidone (325); benalaxyl (56); benalaxyl-M; benomyl (62); bitertanol (84); boscalid (88); carboxin (120); carpropamid (122); copper (diverse salts); copper ammoniumcarbonate; copper octanoate (170); copper oleate; copper sulphate (87; 172; 173); copper hydroxide (169); cyazofamid (185); cymoxanil (200); diethofencarb (245); dithianon (279); fenhexamide (334); fenoxycarb (340); fluazinam (363); flutolanil (396); folpet (400); guazatine (422); hymexazole; iprodione (470); lufenuron (490); mancozeb (496); metalaxyl (516); mefenoxam (517); metrafenone; nuarimol (587); paclobutrazol (612); pencycuron (620); penthiopyrad; procymidone (660); pyroquilon (710); quinoxyfen (715); silthiofam (729); sulfur (754); thiabendazole (790); thiram (804); triazoxide (821); tricyclazole (828); proquinazid (682); captan (114);

a compound of formula B-2

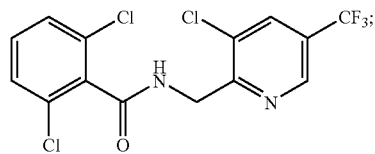
(B-2)

a compound of formula B-3

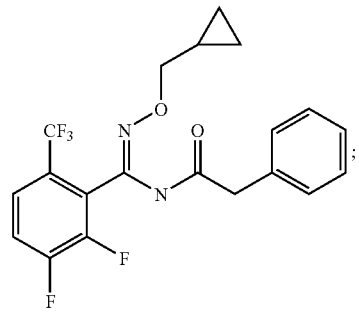
(B-3)

a compound of formula B-4

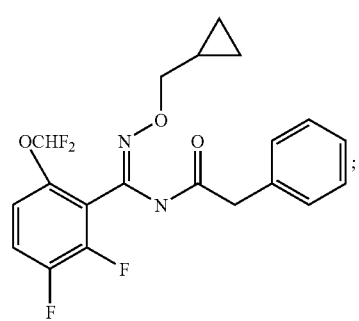
(B-4)

a compound of formula B-8

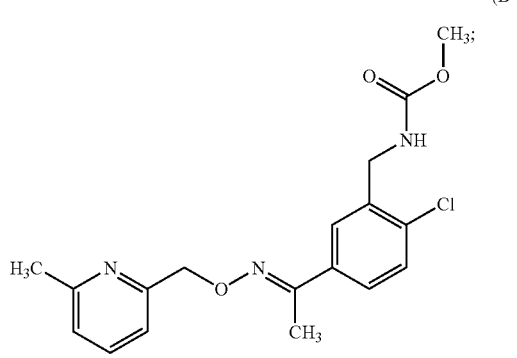
(B-8)

a compound of formula B-9

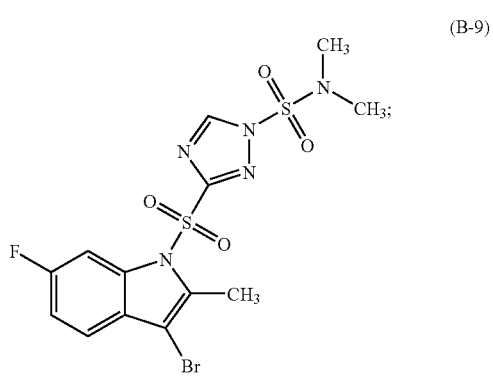
(B-9)

a racemic compound of formula F-7 (trans)

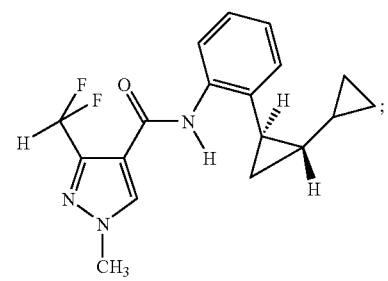
(F-7)

a racemic compound of formula F-8 (cis)

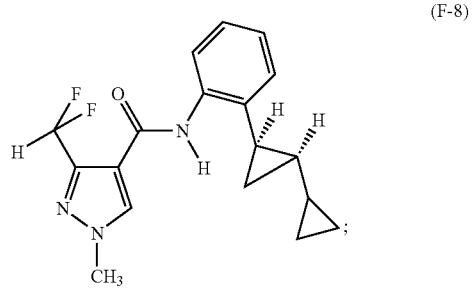
(F-8)

a compound of formula F-9

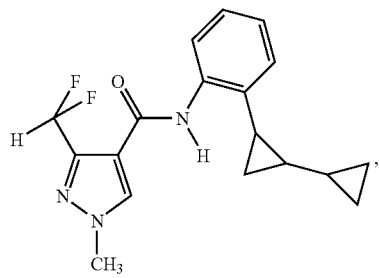
(F-9)

which represents a mixture of racemic compounds of formula F-7 (trans) and F-8 (cis), wherein the ratio of racemic compounds of formula F-7 (trans) to racemic compounds of formula F-8 (cis) is from 2:1 to 100:1;
trinexapac-Ethyl (841); chlormequat chloride (137); ethephon (307); acibenzolar-5-methyl (6); mepiquat chloride (509);
abamectin (1); emamectin benzoate (291); tefluthrin (769); thiamethoxam (792);

a compound of formula A-1

(A-1)

a compound of formula A-2

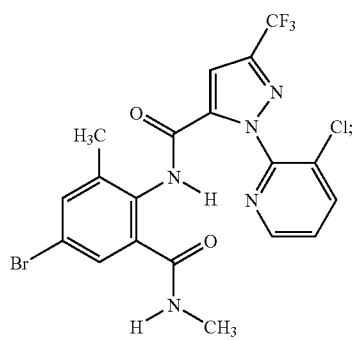
(A-2)

a compound of formula A-3

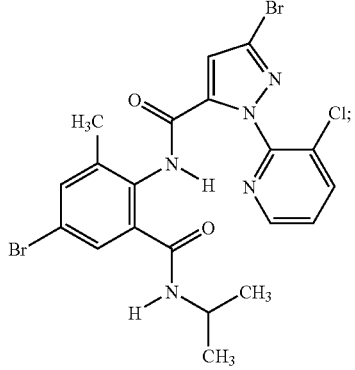
(A-3)

a compound of formula A-4

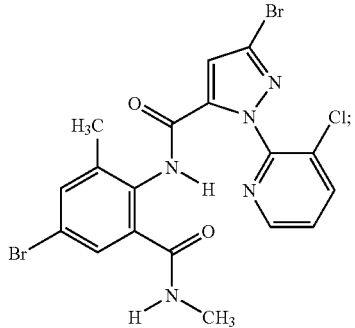
(A-4)

a compound of formula A-5

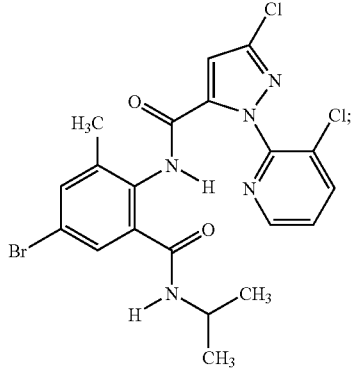
(A-5)

a compound of formula A-6

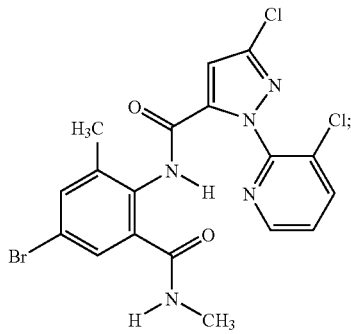
(A-6)

a compound of formula A-7

(A-7)

a compound of formula A-8

(A-8)

a compound of formula A-9

(A-9)

a compound of formula A-10

(A-10)

a compound of formula A-11

(A-11)

a compound of formula A-12

(A-12)

a compound of formula A-13

(A-13)

a compound of formula A-14

(A-14)

a compound of formula A-15
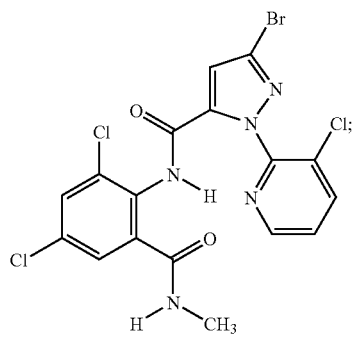
(A-15)
a compound of formula A-15A
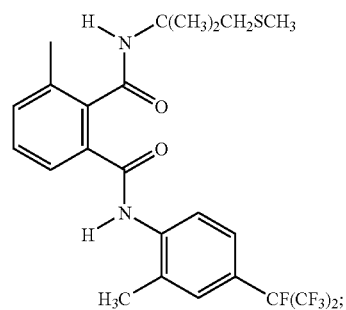
(A-15A)
a compound of formula (A-16)
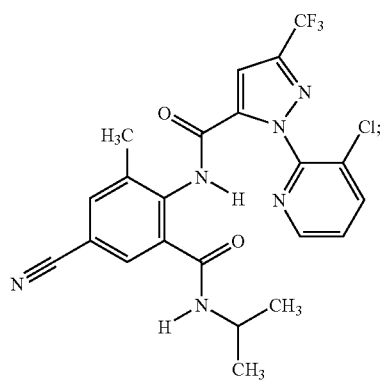
(A-16)
a compound of formula (A-17)
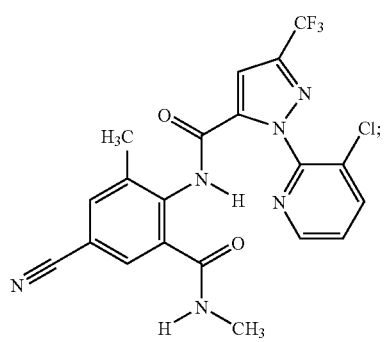
(A-17)
a compound of formula (A-18)
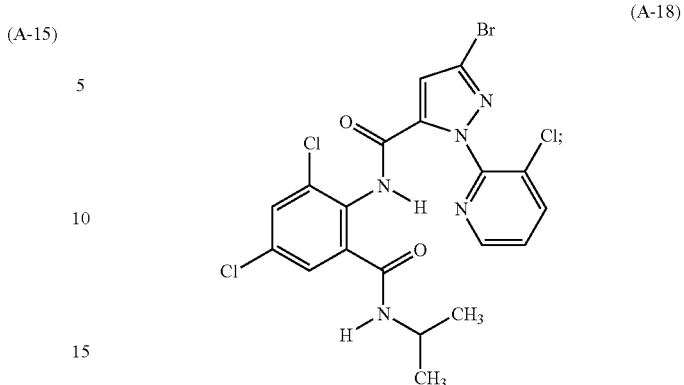
(A-18)
a compound of formula (A-19)
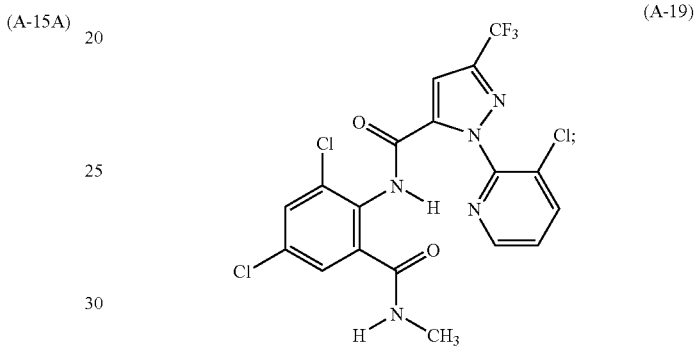
(A-19)
a compound of formula (A-20)
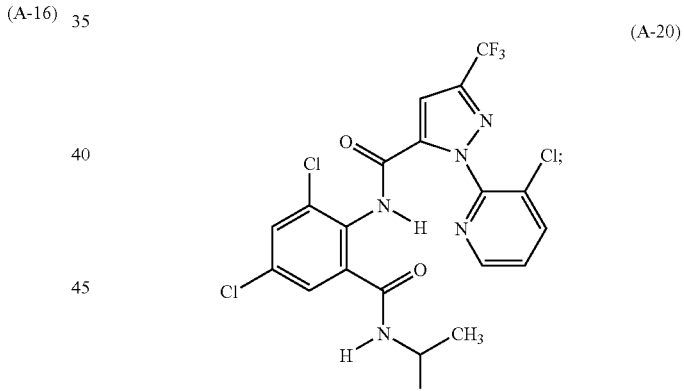
(A-20)
a compound of formula (A-21)
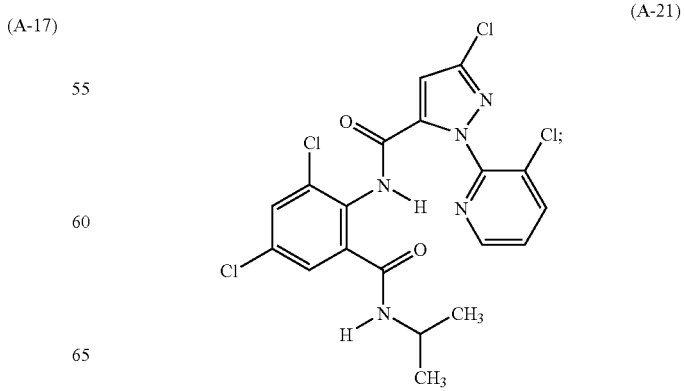
(A-21)

a compound of formula (A-22)

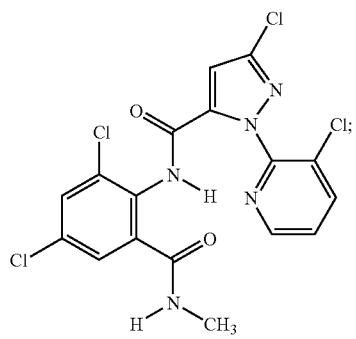
(A-22)

a compound of formula (A-23)

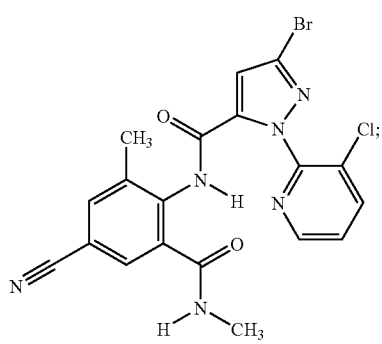
(A-23)

a compound of formula (A-24)

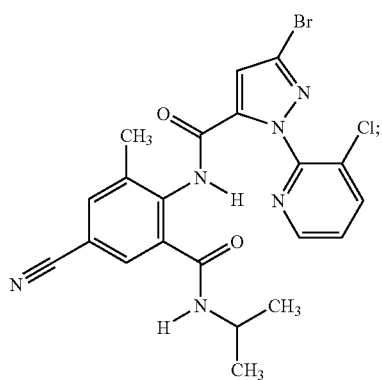
(A-24)

a compound of formula (A-25)

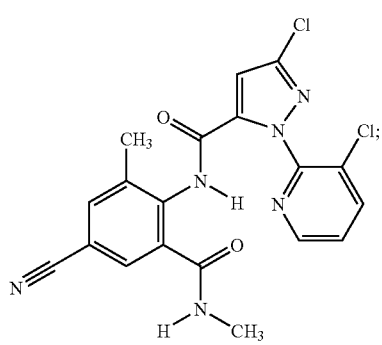
(A-25)

and a compound of formula (A-26)

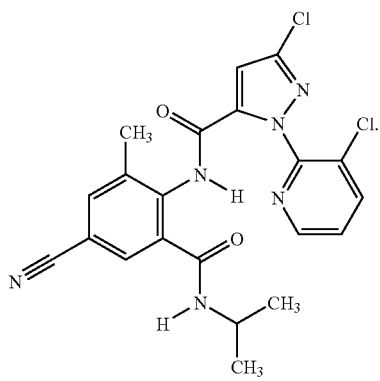
(A-26)

It has now been found, surprisingly, that the active ingredient mixture according to the invention not only brings about the additive enhancement of the spectrum of action with respect to the phytopathogen to be controlled that was in principle to be expected but achieves a synergistic effect which extends the range of action of the component (A) and of the component (B) in two ways. Firstly, the rates of application of the component (A) and of the component (B) are lowered whilst the action remains equally good. Secondly, the active ingredient mixture still achieves a high degree of phytopathogen control even where the two individual components have become totally ineffective in such a low application rate range. This allows, on the one hand, a substantial broadening of the spectrum of phytopathogens that can be controlled and, on the other hand, increased safety in use.

However, besides the actual synergistic action with respect to fungicidal activity, the pesticidal compositions according to the invention also have further surprising advantageous properties which can also be described, in a wider sense, as synergistic activity. Examples of such advantageous properties that may be mentioned are: a broadening of the spectrum of fungicidal activity to other phytopathogens, for example to resistant strains; a reduction in the rate of application of the active ingredients; synergistic activity against animal pests, such as insects or representatives of the order Acarina; a broadening of the spectrum of pesticidal activity to other animal pests, for example to resistant animal pests; adequate pest control with the aid of the compositions according to the invention, even at a rate of application at which the individual compounds are totally ineffective; advantageous behaviour during formulation and/or upon application, for example upon grinding, sieving, emulsifying, dissolving or dispensing; increased storage stability; improved stability to light; more advantageuos degradability; improved toxicological and/or ecotoxicological behaviour; improved characteristics of the useful plants including: emergence, crop yields, more developed root system, tillering increase, increase in plant height, bigger leaf blade, less dead basal leaves, stronger tillers, greener leaf colour, less fertilizers needed, less seeds needed, more productive tillers, earlier flowering, early grain maturity, less plant verse (lodging), increased shoot growth, improved plant vigor, and early germination; or any other advantages familiar to a person skilled in the art.

The alkyl groups appearing in the substituent definitions may be straight-chain or branched and are, for example, methyl, ethyl, n-propyl, isopropyl, n-butyl, sec-butyl, isobutyl, tert-butyl, pentyl, hexyl and the branched isomers of pentyl and hexyl, preferred alkyl groups are methyl, isopropyl and tert-butyl, the most preferred alkyl group is isopropyl.

The compounds of formula I occur in different stereoisomeric forms, which are described in formulae $I_I$ and $I_{II}$:

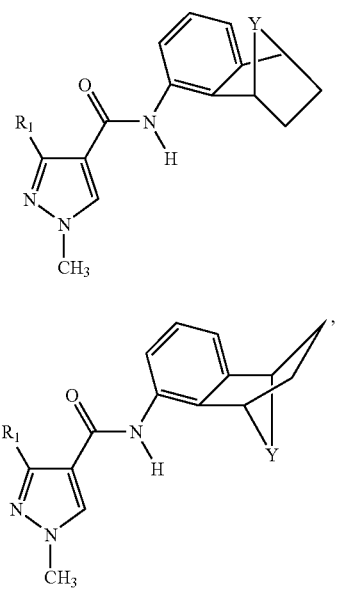

wherein $R_1$ and Y are as defined under formula I. The invention covers all such stereoisomers and mixtures thereof in any ratio.

Since compounds of formula I may also contain asymmetric carbon atoms in the definition of the substituent Y, all the stereoisomers, all syn- and anti-forms and all chiral <R> and <S> forms are also included.

The components (B) are known. Where the components (B) are included in "The Pesticide Manual" [The Pesticide Manual—A World Compendium; Thirteenth Edition; Editor: C. D. S. Tomlin; The British Crop Protection Council], they are described therein under the entry number given in round brackets hereinabove for the particular component (B); for example, the compound "abamectin" is described under entry number (1). Where "[CCN]" is added hereinabove to the particular component (B), the component (B) in question is included in the "Compendium of Pesticide Common Names", which is accessible on the internet [A. Wood; Compendium of Pesticide Common Names, Copyright © 1995-2004]; for example, the compound "acetoprole" is described under the internet address http://www.alanwood.net/pesticides/acetoprole.html.

Most of the components (B) are referred to hereinabove by a so-called "common name", the relevant "ISO common name" or another "common name" being used in individual cases. If the designation is not a "common name", the nature of the designation used instead is given in round brackets for the particular component (B); in that case, the IUPAC name, the IUPAC/Chemical Abstracts name, a "chemical name", a "traditional name", a "compound name" or a "development code" is used or, if neither one of those designations nor a "common name" is used, an "alternative name" is employed.

The following components B) are registered under a CAS-Reg. No.: aldimorph (CAS 91315-15-0); hymexazole (CAS 10004-44-1); copper Ammoniumcarbonate (CAS 33113-08-5); copper oleate (CAS 1120-44-1); benalaxyl-M (CAS 98243-83-5); metrafenone (CAS 220899-03-6) and penthiopyrad (CAS 183675-82-3). The compounds of formulae F-7, F-8 and F-9 are described in WO 03/74491. The compounds of formulae A-1, A-2, A-3, A-4, A-5, A-6, A-7, A-8, A-9, A-10, A-11, A-12, A-13, A-14, A-15, A-18, A-19, A-20, A-21 and A-22 are described in WO 03/15519. The compound of formula A-15A is described in EP-A-1 006 107. The compounds of formulae A-16, A-17, A-23, A-24, A-25 and A-26 are described in WO 04/67528. The compound of formula F-1 is described in WO 01/87822. Compounds of formula B-1A and the compound of formula B-1 are described in WO 98/46607. The compound of formula B-2 is described in WO 99/42447. The compound of formula B-3 is described in WO 96/19442. The compound of formula B-4 is described in WO 99/14187. The compound of formula B-5 is described in U.S. Pat. No. 5,945,423 and WO 94/26722. The compound of formula B-6 is described in EP-0-936-213. The compound of formula B-7 is described in U.S. Pat. No. 6,020,332, CN-1-167-568, CN-1-155-977 and EP-0-860-438. The compound of formula B-8 is registered under CAS-Reg. No.: 325156-49-8 and is also known as Pyribencarb. The compound of formula B-9 is registered under CAS-Reg. No.: 348635-87-0 and is also known as Ambromdole or Amisulbrom.

According to the instant invention, a "racemic compound" means a mixture of two enantiomers in a ratio of substantially 50:50 of the two enantiomers.

Throughout this document the expression "combination" stands for the various combinations of components A) and B), for example in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the components A) and B) is not essential for working the present invention.

The combinations according to the invention may also comprise more than one of the active components B), if, for example, a broadening of the spectrum of phytopathogenic disease control is desired. For instance, it may be advantageous in the agricultural practice to combine two or three components B) with any of the compounds of formula I, or with any preferred member of the group of compounds of formula I.

A preferred embodiment of the present invention is represented by those combinations which comprise as component A) a compound of the formula I, wherein $R_1$ is difluoromethyl or trifluoromethyl; Y is —$CHR_2$— and $R_2$ is hydrogen or $C_1$-$C_6$alkyl; and one component B) as described above.

A preferred embodiment of the present invention is represented by those combinations which comprise as component A) a compound of the formula I, wherein $R_1$ is trifluoromethyl; and one component B) as described above.

A preferred embodiment of the present invention is represented by those combinations which comprise as component A) a compound of the formula I, wherein $R_1$ is difluoromethyl; and one component B) as described above.

A preferred embodiment of the present invention is represented by those combinations which comprise as component A) a compound of the formula I, wherein $R_1$ is difluoromethyl; and $R_2$ is $C_1$-$C_6$alkyl, and one component B) as described above.

A preferred embodiment of the present invention is represented by those combinations which comprise as component A) a compound of the formula I, wherein $R_1$ is difluoromethyl, Y is —$CHR_2$— and $R_2$ is isopropyl; and one component B) as described above. Within this embodiment of the present invention compounds of formula I occur in different stereoisomeric forms, which are described as the single enantiomers of formulae $I_{III}$, $I_{IV}$, $I_V$ and $I_{VI}$:

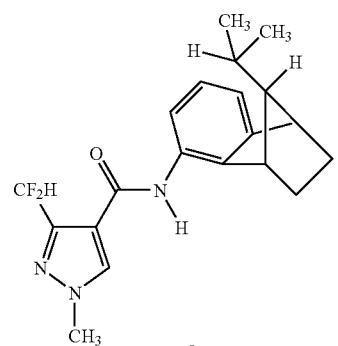

I_III

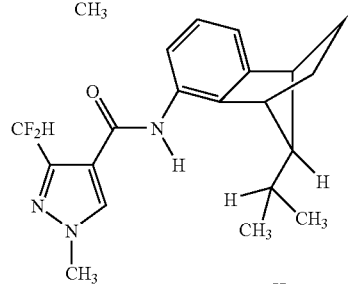

I_IV

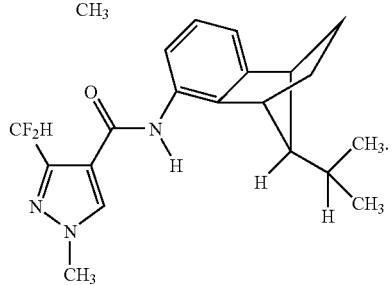

I_VI

The invention covers all such single enantiomers and mixtures thereof in any ratio.

The compounds of formula I and their manufacturing processes starting from known and commercially available compounds are described in WO 04/035589. In particular it is described in WO 04/035589 that the preferred compound of formula I, wherein $R_1$ is difluoromethyl, Y is —$CHR_2$— and $R_2$ is isopropyl, which is represented by the structure $I^a$, (I^a)

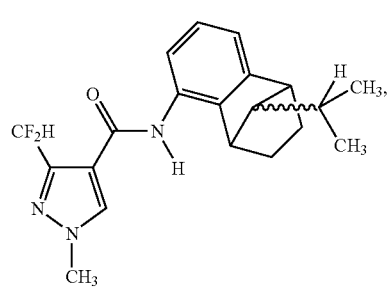

can be prepared by reacting an acid chloride of formula II (II)

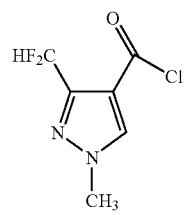

with an amine of formula III (III)

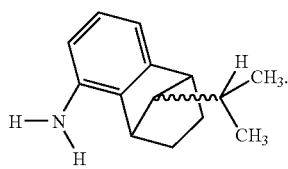

Acids of formula IV (IV)

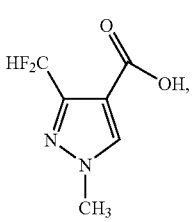

are used for the production of the acid chlorides of formula II, via reaction steps as described in WO 04/035589. When producing the acids of the formula IV using said methology impurities of formula IVA, IVB and/or IVC may be formed:

(IVA)

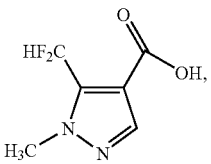

(IVB)

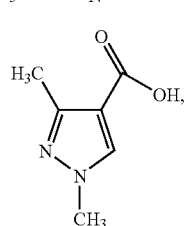

(IVC)

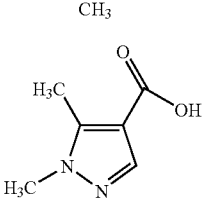

When applying the described manufacturing processes for compounds of formula I$^a$, some/all of those impurities may be carried through different steps of said manufacturing processes. This then can lead to the formation of the corresponding acid chlorides (IIA, IIB and/or IIC)

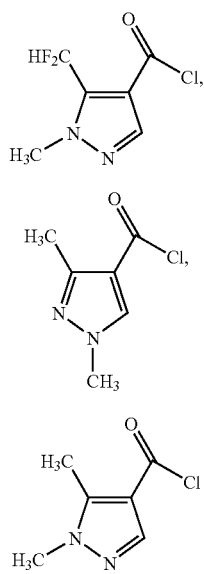

(IIA)

(IIB)

(IIC)

and to the formation of the corresponding amides (VA, VB and/or VC)

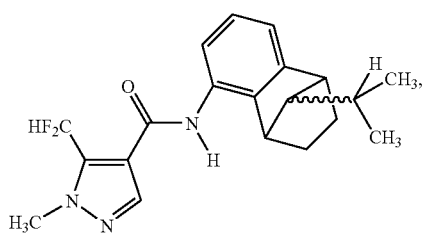

(VA)

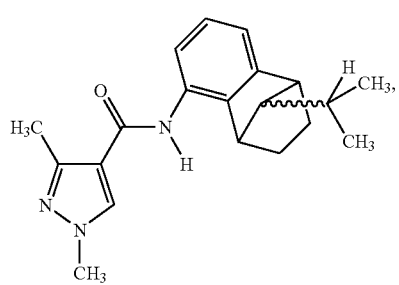

(VB)

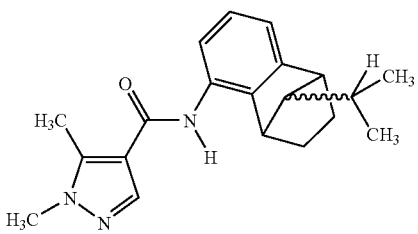

(VC)

as further impurities of compounds of formula I$^a$. The presence/amount of said impurities in preparations of said compounds of formula I$^a$ varies dependent on purification steps used.

Amines of formula III$_B$

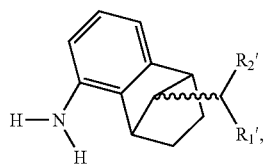

(III$_B$)

wherein $R_1'$ and $R_2'$ are both independently hydrogen or $C_1$-$C_5$alkyl, but $R_1'$ and $R_2'$ are both chosen in a way that the grouping —CHR$_1'$R$_2'$ altogether is a $C_1$-$C_6$alkyl group. Said grouping —CHR$_1'$R$_2'$ represents a preferred definition of the substituent $R_2$ of compounds of formula I.

Said amines of formula III$_B$ can be produced according to scheme 1.

Scheme 1: Synthesis of III$_B$ using 6-nitroanthranilic acid

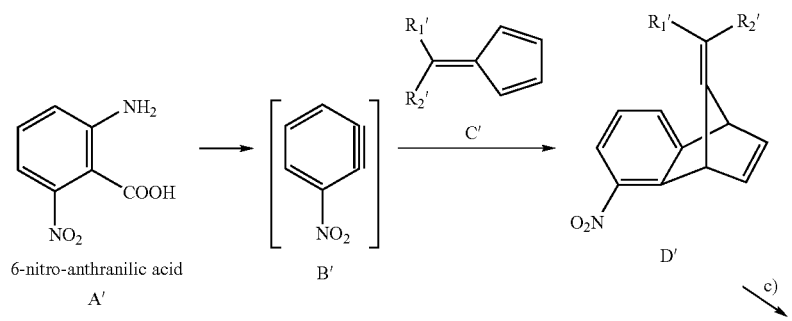

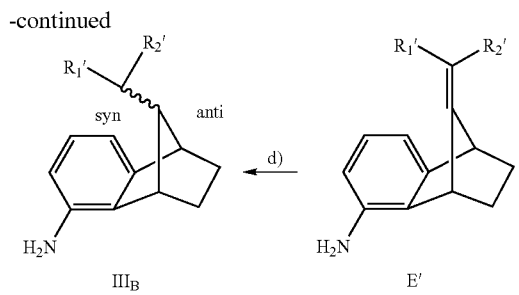

9-Alkylidene-5-nitro-benzonorbornadienes of formula D', wherein $R_1'$ and $R_2'$ are as defined for compounds of formula $III_B$, can be synthesized through Diels-Alder addition of an in situ generated benzyne B' [for example starting from a 6-nitroanthranilic acid of formula (A') by diazotation with i-amyl or t-butyl nitrite], as described by L. Paquette et al, *J. Amer. Chem. Soc.* 99, 3734 (1977) or from other suitable precursors (see H. Pellissier et al. *Tetrahedron*, 59, 701 (2003), R. Muneyuki and H. Tanida, *J. Org. Chem.* 31, 1988 (1966)] to a 6-alkyl- or 6,6-dialkylfulvene according to or by analogy to R. Muneyuki and H. Tanida, *J. Org. Chem.* 31, 1988 (1966), P. Knochel et al, *Angew. Chem.* 116, 4464 (2004), J. W. Coe et al, *Organic Letters* 6, 1589 (2004), L. Paquette et al, *J. Amer. Chem. Soc.* 99, 3734 (1977), R. N. Warrener et al. *Molecules*, 6, 353 (2001), R. N. Warrener et al. *Molecules*, 6, 194 (2001).

Suitable aprotic solvents for this step are for example diethyl ether, butyl methyl ether, ethyl acetate, dichloromethane, acetone, tetrahydrofurane, toluene, 2-butanone or dimethoxyethane. Reaction temperatures range from room temperature to 100° C., preferably 35-80° C. 6-Alkyl- or 6,6-dialkylfulvenes of formula C' are available according to M. Neuenschwander et al, *Helv. Chim. Acta*, 54, 1037 (1971), ibid 48, 955 (1965). R. D. Little et al, *J. Org. Chem.* 49, 1849 (1984), 1. Erden et al, *J. Org. Chem.* 60, 813 (1995) and S. Collins et al, *J. Org. Chem.* 55, 3395 (1990).

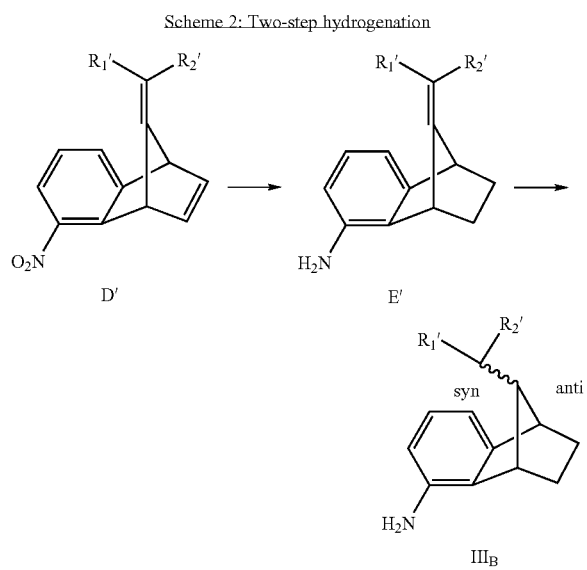

Anilines of formula E' may be obtained according to scheme 2 by partial hydrogenolysis of D', for example by interrupting $H_2$ uptake after 4 equivalents. Suitable solvents include tetrahydrofurane, ethyl acetate, methanol, ethanol, toluene or benzene and others. Catalysts are for example Ra/Ni, Rh/C or Pd/C. Pressure: atmospheric pressure or pressure up to 6 bar, preferentially atmospheric pressure. Temperatures range from room temperature or up to 50° C., preferentially 20-30° C.

Anilines of formula $III_B$ may be obtained from anilines of formula E' by hydrogenation. Suitable solvents are for example tetrahydrofurane, methanol, ethanol, toluene, dichloromethane, ethyl acetate. Preferred solvents are tetrahydrofurane and methanol. Temperatures range from 10 to 50° C., preferentially 20-30° C., more preferred room temperature. Pressure: atmospheric pressure to 150 bar, preferred is atmospheric pressure to 100 bar. The choice of catalyst influences the syn/anti-ratio. Catalysts such as Rh/C, $Rh/Al_2O_3$, $Rh_2O_3$, $Pt/C$ or $PtO_2$ result in syn-enrichment (preferred Rh/C). Catalysts such as Ra/Ni, Ir(COD)Py(Pcy) or Pd/C result in anti-enrichment (preferred Pd/C).

Anilines of formula $III_B$ may also be produced according to scheme 3.

Scheme 3: One-pot hydrogenation

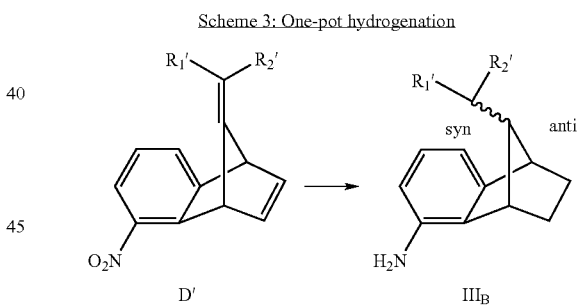

Anilines $III_B$ may be obtained by a one-pot reaction from compounds of formula D' via exhaustive hydrogenation (scheme 3). Suitable solvents are for example tetrahydrofurane, methanol, ethanol, toluene or ethyl acetate. Preferred solvents are tetrahydrofurane or methanol. Temperatures range from room temperature to 50° C., preferred is room temperature to 30° C., most preferred room temperature. Pressure: atmospheric pressure to 100 bar, more preferred 50 bar, even more preferred 20 bar, most preferred atmospheric pressure to 4-6 bar. Likewise, as described for scheme 2 above, the choice of catalyst influences the syn/anti-ratio. Catalysts such as Rh/C, $Rh/Al_2O_3$, $Rh_2O_3$, $Pt/C$ or $PtO_2$ result in syn-enrichment. Catalysts such as Pd/C, Ir(COD)Py(Pcy) or Ra/Ni result in anti-enrichment (preferred catalyst is Pd/C).

The following compounds of formula D' are useful for manufacturing preferred compounds of formula I.

TABLE 1

Compounds of formula D'

(D')

| Cpd No. | $R_1'$ | $R_2'$ | Remarks |
|---|---|---|---|
| Z1.01 | H | $CH_3$ | E/Z-mixture |
| Z1.02 | H | $C_2H_5$ | E/Z-mixture |
| Z1.03 | H | $n-C_3H_7$ | E/Z-mixture |
| Z1.04 | H | $i-C_3H_7$ | E/Z-mixture |
| Z1.05 | H | $c-C_3H_5$ | E/Z-mixture |
| Z1.06 | H | $n-C_4H_9$ | E/Z-mixture |
| Z1.07 | H | $i-C_4H_9$ | E/Z-mixture |
| Z1.08 | H | $sec-C_4H_9$ | E/Z-mixture |
| Z1.09 | H | $t-C_4H_9$ | E/Z-mixture |
| Z1.10 | H | $n-C_5H_{11}$ | E/Z-mixture |
| Z1.11 | $CH_3$ | $CH_3$ | |
| Z1.12 | $C_2H_5$ | $C_2H_5$ | |
| Z1.13 | $CH_3$ | $C_2H_5$ | E/Z-mixture |
| Z1.14 | $CH_3$ | $n-C_3H_7$ | E/Z-mixture |
| Z1.15 | $CH_3$ | $i-C_3H_7$ | E/Z-mixture |
| Z1.16 | $CH_3$ | $c-C_3H_5$ | E/Z-mixture |
| Z1.17 | H | H | |

The following compounds of formula E' are useful for manufacturing preferred compounds of formula I.

TABLE 2

Compounds of formula E'

(E')

| Cpd No. | $R_1'$ | $R_2'$ | Remarks |
|---|---|---|---|
| Z2.01 | H | $CH_3$ | E/Z-mixture |
| Z2.02 | H | $C_2H_5$ | E/Z-mixture |
| Z2.03 | H | $n-C_3H_7$ | E/Z-mixture |
| Z2.04 | H | $i-C_3H_7$ | E/Z-mixture |
| Z2.05 | H | $c-C_3H_5$ | E/Z-mixture |
| Z2.06 | H | $n-C_4H_9$ | E/Z-mixture |
| Z2.07 | H | $i-C_4H_9$ | E/Z-mixture |
| Z2.08 | H | $sec-C_4H_9$ | E/Z-mixture |
| Z2.09 | H | $t-C_4H_9$ | E/Z-mixture |
| Z2.10 | H | $n-C_5H_{11}$ | E/Z-mixture |
| Z2.11 | $CH_3$ | $CH_3$ | |
| Z2.12 | $C_2H_5$ | $C_2H_5$ | |
| Z2.13 | $CH_3$ | $C_2H_5$ | E/Z-mixture |
| Z2.14 | $CH_3$ | $n-C_3H_7$ | E/Z-mixture |
| Z2.15 | $CH_3$ | $i-C_3H_7$ | E/Z-mixture |
| Z2.16 | $CH_3$ | $c-C_3H_5$ | E/Z-mixture |
| Z2.17 | H | H | |

The following compounds of formula $III_B$ are useful for manufacturing preferred compounds of formula I.

TABLE 3

Compounds of formula $III_B$ $(III_B)$

| Cpd No. | $R_1'$ | $R_2'$ | Remarks |
|---|---|---|---|
| Z3.01 | H | $CH_3$ | syn/anti-mixture |
| Z3.02 | H | $C_2H_5$ | syn/anti-mixture |
| Z3.03 | H | $n-C_3H_7$ | syn/anti-mixture |
| Z3.04 | H | $i-C_3H_7$ | syn/anti-mixture |
| Z3.05 | H | $c-C_3H_5$ | syn/anti-mixture |
| Z3.06 | H | $n-C_4H_9$ | syn/anti-mixture |
| Z3.07 | H | $i-C_4H_9$ | syn/anti-mixture |
| Z3.08 | H | $sec-C_4H_9$ | syn/anti-mixture |
| Z3.09 | H | $t-C_4H_9$ | syn/anti-mixture |
| Z3.10 | H | $n-C_5H_{11}$ | syn/anti-mixture |
| Z3.11 | $CH_3$ | $CH_3$ | syn/anti-mixture |
| Z3.12 | $C_2H_5$ | $C_2H_5$ | syn/anti-mixture |
| Z3.13 | $CH_3$ | $C_2H_5$ | syn/anti-mixture |
| Z3.14 | $CH_3$ | $n-C_3H_7$ | syn/anti-mixture |
| Z3.15 | $CH_3$ | $i-C_3H_7$ | syn/anti-mixture |
| Z3.16 | $CH_3$ | $c-C_3H_5$ | syn/anti-mixture |
| Z3.17 | H | H | syn/anti-mixture |

The following examples illustrate the production of compounds of formula $III_B$.

a) Benzyne Adduct

EXAMPLE H1

9-Isopropylidene-5-nitro-benzonorbornadiene (Cpd No. Z1.11)

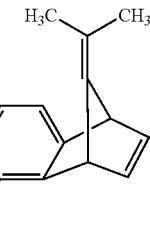

A mixture of 6-nitroanthranilic acid (110.4 g, 0.6 mol) and 6,6-dimethylfulvene (98.5 g, 1.5 eq.) in 700 ml dimethoxyethane was added dropwise to a solution of t-butyl nitrite (96.3 g, 1.4 eq.) in 2 liter 1,2-dimethoxyethane under $N_2$-atmosphere at 72° C. within 20 minutes. A vigorous formation of gas started immediately and the temperature rose to 79° C. Gas formation ceased after 30 min. After 3 h at reflux temperature the mixture was cooled to room temperature, evaporated and purified on silica gel in hexane-ethyl acetate 95:5 resulting in 76.7 g of 9-isopropylidene-5-nitro-benzonorbornadiene as a yellow solid (m.p. 94-95° C.). $^1$H-NMR (CDCl3), ppm: 7.70 (d, 1H), 7.43 (d, 1H), 7.06 (t, 1H), 6.99 (m, 2H), 5.34 (brd s, 1H), 4.47 (brd s, 1H), 1.57 (2 d, 6H). $^{13}$C-NMR (CDCl$_3$), ppm: 159.83, 154.30, 147.33, 144.12, 142.89, 141.93, 125.23 (2×), 119.32, 105.68, 50.51, 50.44, 19.05, 18.90.

b) Two-Step Hydrogenation

EXAMPLE H2

9-Isopropylidene-5-amino-benzonorbornene (Cpd No. Z2.11)

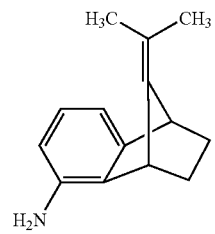

5.0 g 9-isopropylidene-5-nitro-benzonorbornadiene (Cpd No. Z1.11) (22 mmol) were hydrogenated in 50 ml tetrahydrofurane in the presence of 1.5 g 5% Rh/C at 25° C. and atmospheric pressure. After uptake of 4 equivalents of hydrogen (2.01 liter or 102% of theory) the mixture was filtered, evaporated and purified on silica gel in hexane-ethyl acetate-6:1 giving 2.76 g 9-isopropylidene-5-amino-benzonorbornene as a solid (m.p. 81-82° C.; yield: 62.9% of theory). $^1$H-NMR (CDCl3), ppm: 6.90 (t, 1H), 6.67 (d, 1H), 6.46 (d, 1H), 3.77 (m, 1H), 3.73 (m, 1H), 3.35 (brd, exchangeable with D$_2$O, 2H), 1.89 (m, 2H), 1.63 (2 s, 6H), 1.26 (m, 2H). $^{13}$C-NMR (CDCl$_3$), ppm: 148.73, 147.65, 138.30, 131.75, 126.19, 113.12, 110.89, 110.19, 43.97, 39.44, 26.98, 26.06, 19.85, 19.75.

EXAMPLE H3

9-Isopropyl-5-amino-benzonorbornene (Cpd No. Z3.11)

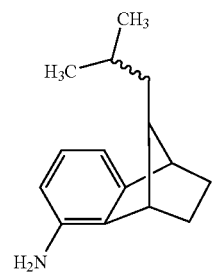

200 mg 9-isopropylidene-5-amino-benzonorbornene (Cpd No. Z2.11) were hydrogenated in the presence of 100 mg 5% Rh/C in 40 ml tetrahydrofurane in a stainless steel autoclave at room temperature at 100 bar resulting in 9-isopropyl-5-amino-benzonorbornene in the form of an oil (syn/anti-ratio 9:1). syn-Epimer: $^1$H-NMR (CDCl$_3$), ppm: 6.91 (t, 1H), 6.64 (d, 1H), 6.48 (d, 1H), 3.54 (brd, exchangeable with D$_2$O, 2H), 3.20 (m, 1H), 3.15 (m, 1H), 1.92 (m, 2H), 1.53 (d, 1H), 1.18 (m, 2H), 1.02 (m, 1H), 0.81 (m, 6H); $^{13}$C-NMR (CDCl3), ppm: 147.73, 140.03, 130.15, 126.41, 113.35, 112.68, 69.00, 46.62, 42.06, 27.74, 26.83, 25.45, 22.32, 22.04; anti-epimer: $^1$H-NMR (CDCl$_3$), ppm: 6.89 (t, 1H), 6.63 (d, 1H), 6.46 (d, 1H), 3.55 (brd, exchangeable with D$_2$O, 2H), 3.16 (m, 1H), 3.13 (m, 1H), 1.87 (m, 2H), 1.48 (d, 1H), 1.42 (m, 1H), 1.12 (m, 2H), 0.90 (m, 6H); $^{13}$C-NMR (CDCl$_3$), ppm: 150.72, 138.74, 133.63, 126.15, 112.94, 111.53, 68.05, 45.21, 40.61, 26.25, 24.47, 23.55, 20.91 (2×). Assignments were made on the basis of NOE-NMR-experiments.

c) One-Pot Hydrogenation:

EXAMPLE H4

9-Isopropyl-5-amino-benzonorbornene (Cpd No. Z3.11) syn-enrichment 35.9 g 9-isopropylidene-5-nitro-benzonorbornadiene (Cpd No. Z1.11) in 400 ml tetrahydrofurane were exhaustively hydrogenated in the presence of 25 g 5% Rh/C over 106 h. Filtration and evaporation of the solvent resulted in 32.15 g 9-isopropyl-5-amino-benzonorbornene (Cpd No. Z3.11) in the form of an oil (syn/anti-ratio 9:1; yield: 97.4% of theory). NMR data: see above.

EXAMPLE H5

9-Isopropyl-5-amino-benzonorbornene (Cpd No. Z3.11): anti-enrichment 41.41 g 9-isopropylidene-5-nitro-benzonorbornadiene (Cpd No. Z10.11) in 1 liter tetrahydrofurane were exhaustively hydrogenated for four hours in the presence of 22 g 5% Pd/C at room temperature and atmospheric pressure. Filtration and evaporation followed by purification on silica gel in hexane-ethyl acetate-7:1 gave 29.91 g 9-isopropyl-5-amino-benzonorbornene (Cpd No. Z3.11) (syn/anti-ratio 3:7; yield: 81.5%) in the form of an oil. NMR data: see above.

A preferred embodiment of the present invention is represented by those combinations which comprise as component A) a compound of formula Ia (syn)

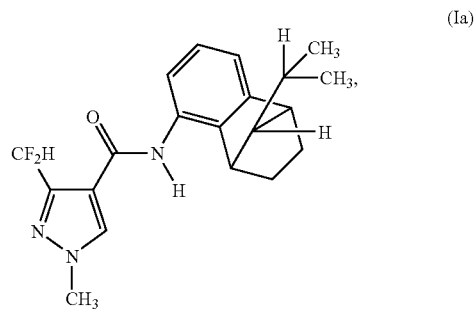

which represents a single enantiomer of formula $I_{III}$, a single enantiomer of formula $I_{IV}$ or a mixture in any ratio of the single enantiomers of formulae $I_{III}$ and $I_{IV}$; and one component B) as described above.

Among this embodiment of the invention preference is given to those combinations which comprise as component A) a racemic compound of the formula Ia (syn), which represents a racemic mixture of the single enantiomers of formulae $I_{III}$ and $I_{IV}$; and one component B) as described above.

A further preferred embodiment of the present invention is represented by those combinations which comprise as component A) a compound of formula Ib (anti)

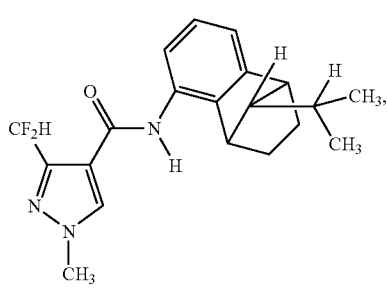

(Ib)

which represents a single enantiomer of formula $I_V$, a single enantiomer of formula $I_{VI}$ or a mixture in any ratio of the single enantiomers of formulae $I_V$ and $I_{VI}$; and one component B) as described above.

A further preferred embodiment of the present invention is represented by those combinations which comprise as component A) a racemic compound of the formula Ib (anti), which represents a racemic mixture of the single enantiomers of formulae $I_V$ and $I_{VI}$; and one component B) as described above.

A further preferred embodiment of the present invention is represented by those combinations which comprise as component A) a compound of formula Ic

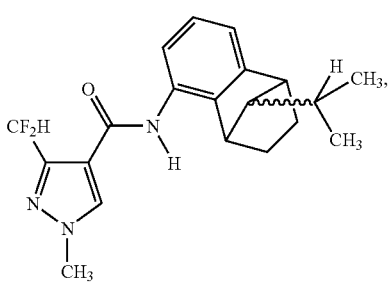

(Ic)

which represents an epimeric mixture of the racemic compounds of formula Ia (syn) and Ib (anti), wherein the ratio of the racemic compound of formula Ia (syn), which represents a racemic mixture of the single enantiomers of formulae $I_{III}$ and $I_{IV}$, to the racemic compound of formula Ib (anti), which represents a racemic mixture of the single enantiomers of formulae $I_V$ and $I_{VI}$, is from 1000:1 to 1:1000; and one component B) as described above.

A further preferred embodiment of the present invention is represented by those combinations which comprise as component A) a compound of formula Ic, which represents an epimeric mixture of the racemic compounds of formula Ia (syn) and Ib (anti), wherein the content of the racemic compound of formula Ia (syn), which represents a racemic mixture of the single enantiomers of formulae $I_{III}$ and $I_{IV}$, is from 80 to 99% by weight, preferrably 85 to 90% by weight; and one component B) as described above.

A further preferred embodiment of the present invention is represented by those combinations which comprise as component A) a compound of formula Ic, which represents an epimeric mixture of the racemic compounds of formula Ia (syn) and Ib (anti), wherein the content of the racemic compound of formula Ib (anti), which represent a racemic mixture of the single enantiomers of formulae $I_V$ and $I_{VI}$, is from 60 to 99% by weight, preferrably 64 to 70% by weight; and one component B) as described above.

A further preferred embodiment of the present invention is represented by those combinations which comprise as component A) a compound of the formula I, wherein $R_1$ is difluoromethyl and $R_2$ is hydrogen; and one component B) as described above. Within this embodiment of the present invention compounds of formula I occur in two enantiomeric forms, which are described as the single enantiomers of formulae $I_{VII}$ and $I_{VIII}$:

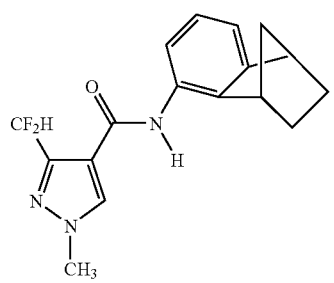

$I_{VII}$

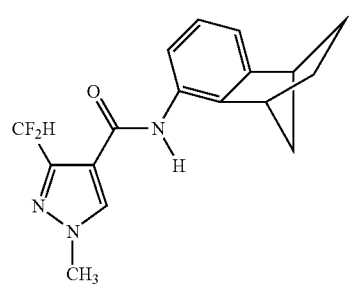

$I_{VIII}$

The invention covers all such single enantiomers and mixtures thereof in any ratio.

A further preferred embodiment of the present invention is represented by those combinations which comprise as component A) a single enantiomer of formula $I_{VII}$; and one component B) as described above.

A further preferred embodiment of the present invention is represented by those combinations which comprise as component A) a single enantiomer of formula $I_{VIII}$; and one component B) as described above.

A further preferred embodiment of the present invention is represented by those combinations which comprise as component A) a compound of formula Id

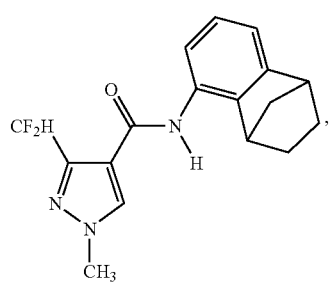

(Id)

which represents a mixture of the single enantiomers of formulae $I_{VII}$ and $I_{VIII}$,
wherein the ratio of the single enantiomer of formula $I_{VII}$ to the single enantiomer of formula $I_{VIII}$ is from 1000:1 to 1:1000; and one component B) as described above.

A further preferred embodiment of the present invention is represented by those combinations which comprise as component A) a compound of the formula I, wherein Y is

and $R_1$ is difluoromethyl; and one component B) as described above. Within this embodiment of the present invention compounds of formula I occur in two enantiomeric forms, which are described as the single enantiomers of formulae $I_{IX}$ and $I_X$:

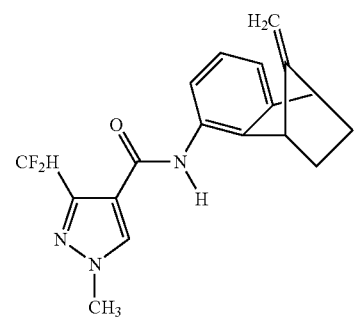

$I_{IX}$

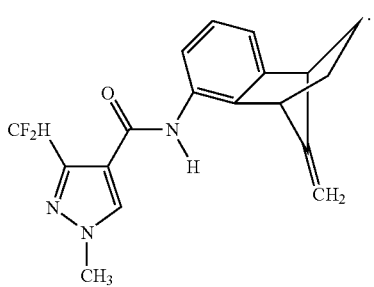

$I_X$

The invention covers all such single enantiomers and mixtures thereof in any ratio.

According to the instant invention, a "racemic mixture" of two enantiomers or a "racemic compound" means a mixture of two enantiomers in a ratio of substantially 50:50 of the two single enantiomers.

Preferred components B) are selected from the group consisting of
a strobilurin fungicide, selected from the group consisting of azoxystrobin, dimoxystrobin, fluoxastrobin, kresoxim-methyl, metominostrobin, orysastrobin, picoxystrobin, pyraclostrobin; trifloxystrobin; and a compound of formula B-6;
an azole fungicide, selected from the group consisting of azaconazole, bromuconazole, cyproconazole, difenoconazole, diniconazole, diniconazole-M, epoxiconazole, fenbuconazole, fluquinconazole, flusilazole, flutriafol, hexaconazole, imazalil, imibenconazole, ipconazole, metconazole, myclobutanil, oxpoconazole, pefurazoate, penconazole, prochloraz, propiconazole, prothioconazole, simeconazole, tebuconazole, tetraconazole, triadimefon, triadimenol, triflumizole, triticonazole, diclobutrazol, etaconazole, furconazole, furconazole-cis and quinconazole;
a phenyl pyrrole fungicide, selected from the group consisting of fenpiclonil and fludioxonil; an anilino-pyrimidine fungicide, selected from the group consisting of cyprodinil, mepanipyrim and pyrimethanil;
a morpholine fungicide, selected from the group consisting of aldimorph, dodemorph, fenpropimorph, tridemorph, fenpropidin, spiroxamine; piperalin and a compound of formula B-7;
a compound of formula F-1; a compound of formula B-1; chlorothalonil; famoxadone; fenamidone; acibenzolar-5-methyl; benalaxyl; benalaxyl-M; benomyl; bitertanol; boscalid; carboxin; carpropamid; copper; cyazofamid; cymoxanil; diethofencarb; dithianon; fenhexamide; fenoxycarb; fluazinam; flutolanil; folpet; guazatine; hymexazole; iprodione; lufenuron; mancozeb; metalaxyl; mefenoxam; metrafenone; nuarimol; paclobutrazol; pencycuron; penthiopyrad; procymidone; pyroquilon; quinoxyfen; silthiofam; sulfur; thiabendazole; thiram; triazoxide; tricyclazole; abamectin; emamectin benzoate; tefluthrin and thiamethoxam.

Preferred components B) are selected from the group consisting of
a strobilurin fungicide, selected from the group consisting of azoxystrobin, fluoxastrobin, picoxystrobin and pyraclostrobin;
an azole fungicide, selected from the group consisting of cyproconazole, difenoconazole, epoxiconazole, flutriafol, metconazole, propiconazole, prothioconazole, tetraconazole; fludioxonil, cyprodinil, fenpropimorph, fenpropidin, a compound of formula F-1; a compound of formula B-1 and Chlorothalonil.

A more preferred component B) is azoxystrobin; picoxystrobin; cyproconazole; difenoconazole; propiconazole; fludioxonil; cyprodinil; fenpropimorph; fenpropidin; a compound of formula F-1; a compound of formula B-1; chlorothalonil, epoxiconazole or prothioconazole.

A further more preferred component B) is azoxystrobin; picoxystrobin; cyproconazole; difenoconazole; propiconazole; fludioxonil; cyprodinil; fenpropimorph; fenpropidin; a compound of formula F-1 or chlorothalonil.

A preferred embodiment of the present invention is represented by those combinations which comprise as component A) a compound of the formula I, wherein $R_1$ is difluoromethyl; and one component B) selected from the group consisting of
a strobilurin fungicide, selected from the group consisting of azoxystrobin, dimoxystrobin, fluoxastrobin, kresoxim-methyl, metominostrobin, orysastrobin, picoxystrobin, pyraclostrobin; trifloxystrobin; and a compound of formula B-6;
an azole fungicide, selected from the group consisting of azaconazole, bromuconazole, cyproconazole, difenoconazole, diniconazole, diniconazole-M, epoxiconazole, fenbuconazole, fluquinconazole, flusilazole, flutriafol, hexaconazole, imazalil, imibenconazole, ipconazole, metconazole, myclobutanil, oxpoconazole, pefurazoate, penconazole, prochloraz, propiconazole, prothioconazole, simeconazole, tebuconazole, tetraconazole, triadimefon, triadimenol, triflumizole, triticonazole, diclobutrazol, etaconazole, furconazole, furconazole-cis and quinconazole;
a phenyl pyrrole fungicide, selected from the group consisting of fenpiclonil and fludioxonil; an anilino-pyrimidine fungicide, selected from the group consisting of cyprodinil, mepanipyrim and pyrimethanil;
a morpholine fungicide, selected from the group consisting of aldimorph, dodemorph, fenpropimorph, tridemorph, fenpropidin, spiroxamine; piperalin and a compound of formula B-7;
a compound of formula F-1; a compound of formula B-1; chlorothalonil; famoxadone; fenamidone; acibenzolar-5-methyl; benalaxyl; benalaxyl-M; benomyl; bitertanol; boscalid; carboxin; carpropamid; copper; cyazofamid; cymoxanil; diethofencarb; dithianon; fenhexamide; fenoxycarb; fluazinam; flutolanil; folpet; guazatine; hymexazole; iprodione; lufenuron; mancozeb; metalaxyl; mefenoxam; metrafenone; nuarimol; paclobutrazol; pencycuron; penthiopyrad; procymidone; pyroquilon; quinoxyfen; silthiofam; sulfur; thiabendazole; thiram; triazoxide; tricyclazole; abamectin; emamectin benzoate; tefluthrin and thiamethoxam.

A preferred embodiment of the present invention is represented by those combinations which comprise as component A) a compound of the formula I, wherein $R_1$ is difluoromethyl; and $R_2$ is $C_1$-$C_6$alkyl, and one component B) selected from the group consisting of
a strobilurin fungicide, selected from the group consisting of azoxystrobin, dimoxystrobin, fluoxastrobin, kresoxim-methyl, metominostrobin, orysastrobin, picoxystrobin, pyraclostrobin; trifloxystrobin; and a compound of formula B-6;
an azole fungicide, selected from the group consisting of azaconazole, bromuconazole, cyproconazole, difenoconazole, diniconazole, diniconazole-M, epoxiconazole, fenbuconazole, fluquinconazole, flusilazole, flutriafol, hexaconazole, imazalil, imibenconazole, ipconazole, metconazole, myclobutanil, oxpoconazole, pefurazoate, penconazole, prochloraz, propiconazole, prothioconazole, simeconazole, tebuconazole, tetraconazole, triadimefon, triadimenol, triflumizole, triticonazole, diclobutrazol, etaconazole, furconazole, furconazole-cis and quinconazole;
a phenyl pyrrole fungicide, selected from the group consisting of fenpiclonil and fludioxonil; an anilino-pyrimidine fungicide, selected from the group consisting of cyprodinil, mepanipyrim and pyrimethanil;
a morpholine fungicide, selected from the group consisting of aldimorph, dodemorph, fenpropimorph, tridemorph, fenpropidin, spiroxamine; piperalin and a compound of formula B-7;
a compound of formula F-1; a compound of formula B-1; chlorothalonil; famoxadone; fenamidone; acibenzolar-5-methyl; benalaxyl; benalaxyl-M; benomyl; bitertanol; boscalid; carboxin; carpropamid; copper; cyazofamid; cymoxanil; diethofencarb; dithianon; fenhexamide; fenoxycarb; fluazinam; flutolanil; folpet; guazatine; hymexazole; iprodione; lufenuron; mancozeb; metalaxyl; mefenoxam; metrafenone; nuarimol; paclobutrazol; pencycuron; penthiopyrad; procymidone; pyroquilon; quinoxyfen; silthiofam; sulfur; thiabendazole; thiram; triazoxide; tricyclazole; abamectin; emamectin benzoate; tefluthrin and thiamethoxam.

A preferred embodiment of the present invention is represented by those combinations which comprise as component A) a compound of the formula I, wherein $R_1$ is difluoromethyl, Y is —$CHR_2$— and $R_2$ is isopropyl; and one component B) selected from the group consisting of a strobilurin fungicide, selected from the group consisting of azoxystrobin, dimoxystrobin, fluoxastrobin, kresoxim-methyl, metominostrobin, orysastrobin, picoxystrobin, pyraclostrobin; trifloxystrobin; and a compound of formula B-6;
an azole fungicide, selected from the group consisting of azaconazole, bromuconazole, cyproconazole, difenoconazole, diniconazole, diniconazole-M, epoxiconazole, fenbuconazole, fluquinconazole, flusilazole, flutriafol, hexaconazole, imazalil, imibenconazole, ipconazole, metconazole, myclobutanil, oxpoconazole, pefurazoate, penconazole, prochloraz, propiconazole, prothioconazole, simeconazole, tebuconazole, tetraconazole, triadimefon, triadimenol, triflumizole, triticonazole, diclobutrazol, etaconazole, furconazole, furconazole-cis and quinconazole;
a phenyl pyrrole fungicide, selected from the group consisting of fenpiclonil and fludioxonil;
an anilino-pyrimidine fungicide, selected from the group consisting of cyprodinil, mepanipyrim and pyrimethanil;
a morpholine fungicide, selected from the group consisting of aldimorph, dodemorph, fenpropimorph, tridemorph, fenpropidin, spiroxamine; piperalin and a compound of formula B-7;
a compound of formula F-1; a compound of formula B-1; chlorothalonil; famoxadone; fenamidone; acibenzolar-5-methyl; benalaxyl; benalaxyl-M; benomyl; bitertanol; boscalid; carboxin; carpropamid; copper; cyazofamid; cymoxanil; diethofencarb; dithianon; fenhexamide; fenoxycarb; fluazinam; flutolanil; folpet; guazatine; hymexazole; iprodione; lufenuron; mancozeb; metalaxyl; mefenoxam; metrafenone; nuarimol; paclobutrazol; pencycuron; penthiopyrad; procymidone; pyroquilon; quinoxyfen; silthiofam; sulfur; thiabendazole; thiram; triazoxide; tricyclazole; abamectin; emamectin benzoate; tefluthrin and thiamethoxam.

A further preferred embodiment of the present invention is represented by those combinations which comprise as component A) a compound of formula Ic

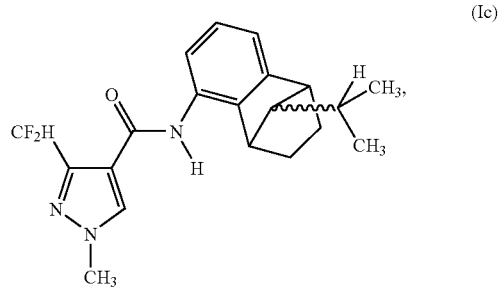

(Ic)

which represents an epimeric mixture of the racemic compounds of formula Ia (syn) and Ib (anti), wherein the ratio of the racemic compound of formula Ia (syn), which represents a racemic mixture of the single enantiomers of formulae $I_{III}$ and $I_{IV}$, to the racemic compound of formula Ib (anti), which represents a racemic mixture of the single enantiomers of formulae $I_V$ and $I_{VI}$, is from 1000:1 to 1:1000; and one component B) selected from the group consisting of a strobilurin fungicide, selected from the group consisting of azoxystrobin, dimoxystrobin, fluoxastrobin, kresoxim-methyl, metominostrobin, orysastrobin, picoxystrobin, pyraclostrobin; trifloxystrobin; and a compound of formula B-6;
an azole fungicide, selected from the group consisting of azaconazole, bromuconazole, cyproconazole, difenoconazole, diniconazole, diniconazole-M, epoxiconazole, fenbuconazole, fluquinconazole, flusilazole, flutriafol, hexaconazole, imazalil, imibenconazole, ipconazole, metconazole, myclobutanil, oxpoconazole, pefurazoate, penconazole, prochloraz, propiconazole, prothioconazole, simeconazole, tebuconazole, tetraconazole, triadimefon, triadimenol, triflumizole, triticonazole, diclobutrazol, etaconazole, furconazole, furconazole-cis and quinconazole;
a phenyl pyrrole fungicide, selected from the group consisting of fenpiclonil and fludioxonil; an anilino-pyrimidine fungicide, selected from the group consisting of cyprodinil, mepanipyrim and pyrimethanil;
a morpholine fungicide, selected from the group consisting of aldimorph, dodemorph, fenpropimorph, tridemorph, fenpropidin, spiroxamine; piperalin and a compound of formula B-7;
a compound of formula F-1; a compound of formula B-1; chlorothalonil; famoxadone; fenamidone; acibenzolar-5-methyl; benalaxyl; benalaxyl-M; benomyl; bitertanol; boscalid; carboxin; carpropamid; copper; cyazofamid; cymoxanil;

diethofencarb; dithianon; fenhexamide; fenoxycarb; fluazinam; flutolanil; folpet; guazatine; hymexazole; iprodione; lufenuron; mancozeb; metalaxyl; mefenoxam; metrafenone; nuarimol; paclobutrazol; pencycuron; penthiopyrad; procymidone; pyroquilon; quinoxyfen; silthiofam; sulfur; thiabendazole; thiram; triazoxide; tricyclazole; abamectin; emamectin benzoate; tefluthrin and thiamethoxam.

A further preferred embodiment of the present invention is represented by those combinations which comprise component A) a compound of formula Ic, which represents an epimeric mixture of the racemic compounds of formula Ia (syn) and Ib (anti), wherein the content of the racemic compound of formula Ia (syn), which represents a racemic mixture of the single enantiomers of formulae $I_{III}$ and $I_{IV}$, is from 80 to 99% by weight, preferrably 85 to 90% by weight; and one component B) selected from the group consisting of
a strobilurin fungicide, selected from the group consisting of azoxystrobin, dimoxystrobin, fluoxastrobin, kresoxim-methyl, metominostrobin, orysastrobin, picoxystrobin, pyraclostrobin; trifloxystrobin; and a compound of formula B-6;
an azole fungicide, selected from the group consisting of azaconazole, bromuconazole, cyproconazole, difenoconazole, diniconazole, diniconazole-M, epoxiconazole, fenbuconazole, fluquinconazole, flusilazole, flutriafol, hexaconazole, imazalil, imibenconazole, ipconazole, metconazole, myclobutanil, oxpoconazole, pefurazoate, penconazole, prochloraz, propiconazole, prothioconazole, simeconazole, tebuconazole, tetraconazole, triadimefon, triadimenol, triflumizole, triticonazole, diclobutrazol, etaconazole, furconazole, furconazole-cis and quinconazole;
a phenyl pyrrole fungicide, selected from the group consisting of fenpiclonil and fludioxonil;
an anilino-pyrimidine fungicide, selected from the group consisting of cyprodinil, mepanipyrim and pyrimethanil;
a morpholine fungicide, selected from the group consisting of aldimorph, dodemorph, fenpropimorph, tridemorph, fenpropidin, spiroxamine; piperalin and a compound of formula B-7;
a compound of formula F-1; a compound of formula B-1; chlorothalonil; famoxadone; fenamidone; acibenzolar-5-methyl; benalaxyl; benalaxyl-M; benomyl; bitertanol; boscalid; carboxin; carpropamid; copper; cyazofamid; cymoxanil; diethofencarb; dithianon; fenhexamide; fenoxycarb; fluazinam; flutolanil; folpet; guazatine; hymexazole; iprodione; lufenuron; mancozeb; metalaxyl; mefenoxam; metrafenone; nuarimol; paclobutrazol; pencycuron; penthiopyrad; procymidone; pyroquilon; quinoxyfen; silthiofam; sulfur; thiabendazole; thiram; triazoxide; tricyclazole; abamectin; emamectin benzoate; tefluthrin and thiamethoxam.

A preferred embodiment of the present invention is represented by those combinations which comprise as component A) a compound of the formula I, wherein $R_1$ is difluoromethyl; and one component B) selected from the group consisting of
a strobilurin fungicide, selected from the group consisting of azoxystrobin, fluoxastrobin, picoxystrobin and pyraclostrobin;
an azole fungicide, selected from the group consisting of cyproconazole, difenoconazole, epoxiconazole, flutriafol, metconazole, propiconazole, prothioconazole, tetraconazole; fludioxonil, cyprodinil, fenpropimorph, fenpropidin, a compound of formula F-1; a compound of formula B-1 and chlorothalonil.

A preferred embodiment of the present invention is represented by those combinations which comprise as component A) a compound of the formula I, wherein $R_1$ is difluoromethyl; and $R_2$ is $C_1$-$C_6$alkyl, and one component B) selected from the group consisting of
a strobilurin fungicide, selected from the group consisting of azoxystrobin, fluoxastrobin, picoxystrobin and pyraclostrobin;
an azole fungicide, selected from the group consisting of cyproconazole, difenoconazole, epoxiconazole, flutriafol, metconazole, propiconazole, prothioconazole, tetraconazole; fludioxonil, cyprodinil, fenpropimorph, fenpropidin, a compound of formula F-1; a compound of formula B-1 and chlorothalonil.

A preferred embodiment of the present invention is represented by those combinations which comprise as component A) a compound of the formula I, wherein $R_1$ is difluoromethyl, Y is —$CHR_2$— and $R_2$ is isopropyl; and one component B) selected from the group consisting of a strobilurin fungicide, selected from the group consisting of azoxystrobin, fluoxastrobin, picoxystrobin and pyraclostrobin;
an azole fungicide, selected from the group consisting of cyproconazole, difenoconazole, epoxiconazole, flutriafol, metconazole, propiconazole, prothioconazole, tetraconazole; fludioxonil, cyprodinil, fenpropimorph, fenpropidin, a compound of formula F-1; a compound of formula B-1 and chlorothalonil.

A further preferred embodiment of the present invention is represented by those combinations which comprise as component A) a compound of formula Ic

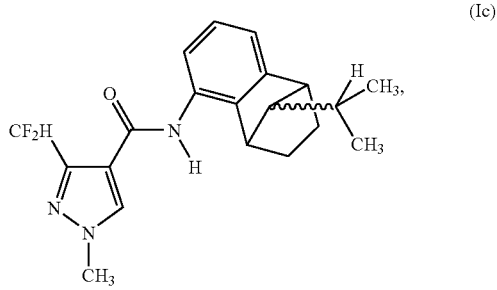

(Ic)

which represents an epimeric mixture of the racemic compounds of formula Ia (syn) and Ib (anti), wherein the ratio of the racemic compound of formula Ia (syn), which represents a racemic mixture of the single enantiomers of formulae $I_{III}$ and $I_{IV}$, to the racemic compound of formula Ib (anti), which represents a racemic mixture of the single enantiomers of formulae $I_V$ and $I_{VI}$, is from 1000:1 to 1:1000; and one component B) selected from the group consisting of
a strobilurin fungicide, selected from the group consisting of azoxystrobin, fluoxastrobin, picoxystrobin and pyraclostrobin;
an azole fungicide, selected from the group consisting of cyproconazole, difenoconazole, epoxiconazole, flutriafol, metconazole, propiconazole, prothioconazole, tetraconazole; fludioxonil, cyprodinil, fenpropimorph, fenpropidin, a compound of formula F-1; a compound of formula B-1 and chlorothalonil.

A further preferred embodiment of the present invention is represented by those combinations which comprise component A) a compound of formula Ic, which represents an epimeric mixture of the racemic compounds of formula Ia (syn) and Ib (anti), wherein the content of the racemic compound of formula Ia (syn), which represents a racemic mixture of the single enantiomers of formulae $I_{III}$ and $I_{IV}$, is from 80 to 99% by weight, preferrably 85 to 90% by weight; and one component B) selected from the group consisting of
a strobilurin fungicide, selected from the group consisting of azoxystrobin, fluoxastrobin, picoxystrobin and pyraclostrobin;
an azole fungicide, selected from the group consisting of cyproconazole, difenoconazole, epoxiconazole, flutriafol, metconazole, propiconazole, prothioconazole, tetraconazole;

fludioxonil, cyprodinil, fenpropimorph, fenpropidin, a compound of formula F-1; a compound of formula B-1 and chlorothalonil.

A further preferred embodiment of the present invention is represented by those combinations which comprise as component A) a compound of formula Ic, which represents an epimeric mixture of the racemic compounds of formula Ia (syn) and Ib (anti), wherein the content of the racemic compound of formula Ib (anti), which represent a racemic mixture of the single enantiomers of formulae $I_V$ and $I_{VI}$, is from 60 to 99% by weight, preferrably 64 to 70% by weight; and one component B) selected from the group consisting of
a strobilurin fungicide, selected from the group consisting of azoxystrobin, fluoxastrobin, picoxystrobin and pyraclostrobin;
an azole fungicide, selected from the group consisting of cyproconazole, difenoconazole, epoxiconazole, flutriafol, metconazole, propiconazole, prothioconazole, tetraconazole; fludioxonil, cyprodinil, fenpropimorph, fenpropidin, a compound of formula F-1; a compound of formula B-1 and chlorothalonil.

A preferred embodiment of the present invention is represented by those combinations which comprise as component A) a compound of the formula I, wherein $R_1$ is difluoromethyl; and one component B) selected from the group consisting of
azoxystrobin; picoxystrobin; cyproconazole; difenoconazole; propiconazole; fludioxonil; cyprodinil; fenpropimorph; fenpropidin; a compound of formula F-1; a compound of formula B-1; chlorothalonil, epoxiconazole and prothioconazole.

A preferred embodiment of the present invention is represented by those combinations which comprise as component A) a compound of the formula I, wherein $R_1$ is difluoromethyl; and $R_2$ is $C_1$-$C_6$alkyl, and one component B) selected from the group consisting of
azoxystrobin; picoxystrobin; cyproconazole; difenoconazole; propiconazole; fludioxonil; cyprodinil; fenpropimorph; fenpropidin; a compound of formula F-1; a compound of formula B-1; chlorothalonil, epoxiconazole and prothioconazole.

A preferred embodiment of the present invention is represented by those combinations which comprise as component A) a compound of the formula I, wherein $R_1$ is difluoromethyl, Y is —$CHR_2$— and $R_2$ is isopropyl; and one component B) selected from the group consisting of azoxystrobin; picoxystrobin; cyproconazole; difenoconazole; propiconazole; fludioxonil; cyprodinil; fenpropimorph; fenpropidin; a compound of formula F-1; a compound of formula B-1; chlorothalonil, epoxiconazole and prothioconazole.

A further preferred embodiment of the present invention is represented by those combinations which comprise as component A) a compound of formula Ic

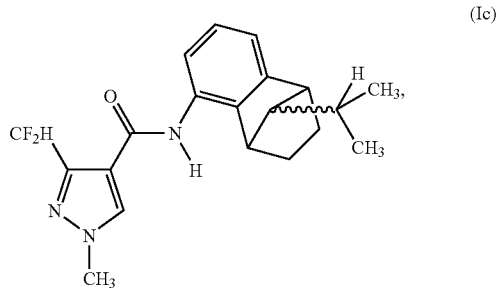

(Ic)

which represents an epimeric mixture of the racemic compounds of formula Ia (syn) and Ib (anti), wherein the ratio of the racemic compound of formula Ia (syn), which represents a racemic mixture of the single enantiomers of formulae $I_{III}$ and $I_{IV}$, to the racemic compound of formula Ib (anti), which represents a racemic mixture of the single enantiomers of formulae $I_V$ and $I_{VI}$, is from 1000:1 to 1:1000; and one component B) selected from the group consisting of azoxystrobin; picoxystrobin; cyproconazole; difenoconazole; propiconazole; fludioxonil; cyprodinil; fenpropimorph; fenpropidin; a compound of formula F-1; a compound of formula B-1; chlorothalonil, epoxiconazole and prothioconazole.

A further preferred embodiment of the present invention is represented by those combinations which comprise as component A) a compound of formula Ic, which represents an epimeric mixture of the racemic compounds of formula Ia (syn) and Ib (anti), wherein the content of the racemic compound of formula Ia (syn), which represents a racemic mixture of the single enantiomers of formulae $I_{III}$ and $I_{IV}$, is from 80 to 99% by weight, preferrably 85 to 90% by weight; and one component B) selected from the group consisting of
azoxystrobin; picoxystrobin; cyproconazole; difenoconazole; propiconazole; fludioxonil; cyprodinil; fenpropimorph; fenpropidin; a compound of formula F-1; a compound of formula B-1; chlorothalonil, epoxiconazole and prothioconazole.

A further preferred embodiment of the present invention is represented by those combinations which comprise as component A) a compound of formula Ic, which represents an epimeric mixture of the racemic compounds of formula Ia (syn) and Ib (anti), wherein the content of the racemic compound of formula Ib (anti), which represent a racemic mixture of the single enantiomers of formulae $I_V$ and $I_{VI}$, is from 60 to 99% by weight, preferrably 64 to 70% by weight; and one component B) selected from the group consisting of
azoxystrobin; picoxystrobin; cyproconazole; difenoconazole; propiconazole; fludioxonil; cyprodinil; fenpropimorph; fenpropidin; a compound of formula F-1; a compound of formula B-1; chlorothalonil, epoxiconazole and prothioconazole.

A preferred embodiment of the present invention is represented by those combinations which comprise as component A) a compound of the formula I, wherein $R_1$ is difluoromethyl; and one component B) selected from the group consisting of
Azoxystrobin; Picoxystrobin; Cyproconazole; Difenoconazole; Propiconazole; Fludioxonil; Cyprodinil; Fenpropimorph; Fenpropidin; a compound of formula F-1 and Chlorothalonil.

A preferred embodiment of the present invention is represented by those combinations which comprise as component A) a compound of the formula I, wherein $R_1$ is difluoromethyl; and $R_2$ is $C_1$-$C_6$alkyl, and one component B) selected from the group consisting of
Azoxystrobin; Picoxystrobin; Cyproconazole; Difenoconazole; Propiconazole; Fludioxonil; Cyprodinil; Fenpropimorph; Fenpropidin; a compound of formula F-1 and Chlorothalonil.

A preferred embodiment of the present invention is represented by those combinations which comprise as component A) a compound of the formula I, wherein $R_1$ is difluoromethyl, Y is —$CHR_2$— and $R_2$ is isopropyl; and one component B) selected from the group consisting of azoxystrobin; picoxystrobin; cyproconazole; difenoconazole; propiconazole; fludioxonil; cyprodinil; fenpropimorph; fenpropidin; a compound of formula F-1 and chlorothalonil.

A further preferred embodiment of the present invention is represented by those combinations which comprise component A) a compound of formula Ic

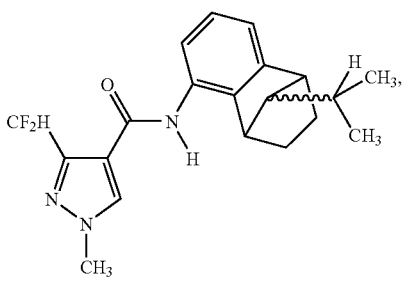

(Ic)

which represents an epimeric mixture of the racemic compounds of formula Ia (syn) and Ib (anti), wherein the ratio of the racemic compound of formula Ia (syn), which represents a racemic mixture of the single enantiomers of formulae $I_{III}$ and $I_{IV}$, to the racemic compound of formula Ib (anti), which represents a racemic mixture of the single enantiomers of formulae $I_V$ and $I_{VI}$, is from 1000:1 to 1:1000; and one component B) selected from the group consisting of azoxystrobin; picoxystrobin; cyproconazole; difenoconazole; propiconazole; fludioxonil; cyprodinil; fenpropimorph; fenpropidin; a compound of formula F-1 and chlorothalonil.

A further preferred embodiment of the present invention is represented by those combinations which comprise as component A) a compound of formula Ic, which represents an epimeric mixture of the racemic compounds of formula Ia (syn) and Ib (anti), wherein the content of the racemic compound of formula Ia (syn), which represents a racemic mixture of the single enantiomers of formulae $I_{III}$ and $I_{IV}$, is from 80 to 99% by weight, preferrably 85 to 90% by weight; and one component B) selected from the group consisting of azoxystrobin; picoxystrobin; cyproconazole; difenoconazole; propiconazole; fludioxonil; cyprodinil; fenpropimorph; fenpropidin; a compound of formula F-1 and chlorothalonil.

A further preferred embodiment of the present invention is represented by those combinations which comprise as component A) a compound of formula Ic, which represents an epimeric mixture of the racemic compounds of formula Ia (syn) and Ib (anti), wherein the content of the racemic compound of formula Ib (anti), which represent a racemic mixture of the single enantiomers of formulae $I_V$ and $I_{VI}$, is from 60 to 99% by weight, preferrably 64 to 70% by weight; and one component B) selected from the group consisting of azoxystrobin; picoxystrobin; cyproconazole; difenoconazole; propiconazole; fludioxonil; cyprodinil; fenpropimorph; fenpropidin; a compound of formula F-1 and chlorothalonil.

In another embodiment of the invention, a preferred component B) is proquinazid; captan; a compound of formula B-2; a compound of formula B-3; a compound of formula B-4; a compound of formula B-8; a compound of formula B-9;
a racemic compound of formula F-7 (trans); racemic compound of formula F-8 (cis); a compound of formula F-9;
trinexapac-ethyl; chlormequat chloride; ethephon; mepiquat chloride;
a compound of formula A-1; a compound of formula A-2; a compound of formula A-3; a compound of formula A-4; a compound of formula A-5; a compound of formula A-6; a compound of formula A-7; a compound of formula A-8; a compound of formula A-9; a compound of formula A-10; a compound of formula A-11; a compound of formula A-12; a compound of formula A-13; a compound of formula A-14; a compound of formula A-15; a compound of formula A-15A; a compound of formula A-16; a compound of formula A-17; a compound of formula A-18; a compound of formula A-19; a compound of formula A-20; a compound of formula A-21; a compound of formula A-22; a compound of formula A-23; a compound of formula A-24; a compound of formula A-25; or a compound of formula A-26.

Within this embodiment, a further preferred component B) is proquinazid; captan; a compound of formula B-2; a compound of formula B-3; a compound of formula B-4; a compound of formula B-8; a compound of formula B-9;
a racemic compound of formula F-7 (trans); racemic compound of formula F-8 (cis); a compound of formula F-9;
trinexapac-ethyl; chlormequat chloride; ethephon; mepiquat chloride;
a compound of formula A-10 or a compound of formula A-23.

Within this embodiment, an even further preferred component B) is a compound of formula B-3 or a compound of formula A-10.

Within this embodiment, a further preferred embodiment of the present invention is represented by those combinations which comprise as component A) a compound of the formula I, wherein $R_1$ is difluoromethyl, Y is —$CHR_2$— and $R_2$ is isopropyl; and one component B) selected from the group consisting of proquinazid; captan; a compound of formula B-2; a compound of formula B-3; a compound of formula B-4; a compound of formula B-8; a compound of formula B-9; a racemic compound of formula F-7 (trans); racemic compound of formula F-8 (cis); a compound of formula F-9;
trinexapac-ethyl; chlormequat chloride; ethephon; mepiquat chloride;
a compound of formula A-1; a compound of formula A-2; a compound of formula A-3; a compound of formula A-4; a compound of formula A-5; a compound of formula A-6; a compound of formula A-7; a compound of formula A-8; a compound of formula A-9; a compound of formula A-10; a compound of formula A-11; a compound of formula A-12; a compound of formula A-13; a compound of formula A-14; a compound of formula A-15; a compound of formula A-15A; a compound of formula A-16; a compound of formula A-17; a compound of formula A-18; a compound of formula A-19; a compound of formula A-20; a compound of formula A-21; a compound of formula A-22; a compound of formula A-23; a compound of formula A-24; a compound of formula A-25; and a compound of formula A-26.

Within this embodiment, a further preferred embodiment of the present invention is represented by those combinations which comprise as component A) a compound of the formula I, wherein $R_1$ is difluoromethyl, Y is —$CHR_2$— and $R_2$ is isopropyl; and one component B) selected from the group consisting of proquinazid; captan; a compound of formula B-2; a compound of formula B-3; a compound of formula B-4; a compound of formula B-8; a compound of formula B-9; a racemic compound of formula F-7 (trans); racemic compound of formula F-8 (cis); a compound of formula F-9;
trinexapac-ethyl; chlormequat chloride; ethephon; mepiquat chloride;
a compound of formula A-10 and a compound of formula A-23.

Within this embodiment, a further preferred embodiment of the present invention is represented by those combinations which comprise as component A) a compound of the formula I, wherein $R_1$ is difluoromethyl, Y is —$CHR_2$— and $R_2$ is isopropyl; and one component B) selected from the group consisting of a compound of formula B-3 and a compound of formula A-10.

The active ingredient combinations are effective against harmful microorganisms, such as microorganisms, that cause phytopathogenic diseases, in particular against phytopathogenic fungi and bacteria.

The active ingredient combinations are effective especially against phytopathogenic fungi belonging to the following classes: Ascomycetes (e.g. *Venturia, Podosphaera, Erysiphe, Monilinia, Mycosphaerella, Uncinula*); Basidiomycetes (e.g. the genus *Hemileia, Rhizoctonia, Phakopsora, Puccinia, Ustilago, Tilletia*); Fungi imperfecti (also known as Deuteromycetes; e.g. *Botrytis, Helminthosporium, Rhynchosporium, Fusarium, Septoria, Cercospora, Alternaria, Pyricularia* and *Pseudocercosporella*); Oomycetes (e.g. *Phytophthora, Peronospora, Pseudoperonospora, Albugo, Bremia, Pythium, Pseudosclerospora, Plasmopara*).

According to the invention "useful plants" typically comprise the following species of plants: grape vines; cereals, such as wheat, barley, rye or oats; beet, such as sugar beet or fodder beet; fruits, such as pomes, stone fruits or soft fruits, for example apples, pears, plums, peaches, almonds, cherries, strawberries, raspberries or blackberries; leguminous plants, such as beans, lentils, peas or soybeans; oil plants, such as rape, mustard, poppy, olives, sunflowers, coconut, castor oil plants, cocoa beans or groundnuts; cucumber plants, such as marrows, cucumbers or melons; fibre plants, such as cotton, flax, hemp or jute; citrus fruit, such as oranges, lemons, grapefruit or mandarins; vegetables, such as spinach, lettuce, asparagus, cabbages, carrots, onions, tomatoes, potatoes, cucurbits or paprika; lauraceae, such as avocados, cinnamon or camphor; maize; tobacco; nuts; coffee; sugar cane; tea; vines; hops; durian; bananas; natural rubber plants; turf or ornamentals, such as flowers, shrubs, broad-leaved trees or evergreens, for example conifers. This list does not represent any limitation.

The term "useful plants" is to be understood as including also useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" is to be understood as including also useful plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins, for example insecticidal proteins from *Bacillus cereus* or *Bacillus popliae*; or insecticidal proteins from *Bacillus thuringiensis*, such as δ-endotoxins, e.g. CryIA(b), CryIA(c), CryIF, CryIF(a2), CryIIA(b), CryIIIA, CryIIIB(b1) or Cry9c, or vegetative insecticidal proteins (VIP), e.g. VIP1, VIP2, VIP3 or VIP3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsine inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example CryIA(b), CryIA(c), CryIF, CryIF(a2), CryIIA(b), CryIIIA, CryIIIB(b1) or Cry9c, or vegetative insecticidal proteins (VIP), for example VIP1, VIP2, VIP3 or VIP3A, expressly also hybrid toxins, truncated toxins and modified toxins. Hybrid toxins are produced recombinantly by a new combination of different domains of those proteins (see, for example, WO 02/15701). An example for a truncated toxin is a truncated CryIA(b), which is expressed in the Bt11 maize from Syngenta Seed SAS, as described below. In the case of modified toxins, one or more amino acids of the naturally occurring toxin are replaced. In such amino acid replacements, preferably non-naturally present protease recognition sequences are inserted into the toxin, such as, for example, in the case of CryIIIA055, a cathepsin-D-recognition sequence is inserted into a CryIIIA toxin (see WO 03/018810)

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. CryI-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and butterflies (Lepidoptera).

Transgenic plants containing one or more genes that code for an insecticidal resistance and express one or more toxins are known and some of them are commercially available. Examples of such plants are: YieldGard® (maize variety that expresses a CryIA(b) toxin); YieldGard Rootworm® (maize variety that expresses a CryIIIB(b1) toxin); YieldGard Plus® (maize variety that expresses a CryIA(b) and a CryIIIB(b1) toxin); Starlink® (maize variety that expresses a Cry9(c) toxin); Herculex I® (maize variety that expresses a CryIF(a2) toxin and the enzyme phosphinothricine N-acetyltransferase (PAT) to achieve tolerance to the herbicide glufosinate ammonium); NuCOTN 33B® (cotton variety that expresses a CryIA(c) toxin); Bollgard I® (cotton variety that expresses a CryIA(c) toxin); Bollgard II® (cotton variety that expresses a CryIA(c) and a CryIIA(b) toxin); VIPCOT® (cotton variety that expresses a VIP toxin); NewLeaf® (potato variety that expresses a CryIIIA toxin); NatureGard® and Protecta®.

Further examples of such transgenic crops are:

1. Bt11 Maize from Syngenta Seeds SAS, Chemin de l'Hobit 27, F-31 790 St. Sauveur, France, registration number C/FR/196105110. Genetically modified *Zea mays* which has been rendered resistant to attack by the European corn borer (*Os-* trinia nubilalis and *Sesamia nonagrioides*) by transgenic expression of a truncated CryIA(b) toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/196105110. Genetically modified *Zea mays* which has been rendered resistant to attack by the European corn borer (*Ostrinia nubilalis* and *Sesamia nonagrioides*) by transgenic expression of a CryIA(b) toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified CryIIIA toxin. This toxin is Cry3A055 modified by insertion of a cathepsin-D-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/0219. MON 863 expresses a CryIIIB(b1) toxin and has resistance to certain Coleoptera insects.

5. IPC 531 Cotton from Monsanto Europe S.A. 270-272 Avenue de Tervuren, B-1150 Brussels, Belgium, registration number C/ES/96102.

6. 1507 Maize from Pioneer Overseas Corporation, Avenue Tedesco, 7 B-1160 Brussels, Belgium, registration number C/NL/00/10. Genetically modified maize for the expression of the protein CryIF for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a CryIA(b) toxin obtained from *Bacillus thuringiensis* subsp. *kurstaki* which brings about tolerance to certain Lepidoptera, include the European corn borer. Transgenic crops of insect-resistant plants are also described in BATS (Zentrum für Biosicherheit und Nachhaltigkeit, Zentrum BATS, Clarastrasse 13, 4058 Basel, Switzerland) Report 2003, (http://bats.ch).

The term "useful plants" is to be understood as including also useful plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defense (so-called "plant disease resistance genes", as described in WO 03/000906).

Useful plants of elevated interest in connection with present invention are cereals; soybean; rice; oil seed rape; pome fruits; stone fruits; peanuts; coffee; tea; strawberries; turf; vines and vegetables, such as tomatoes, potatoes, cucurbits and lettuce.

The term "locus" of a useful plant as used herein is intended to embrace the place on which the useful plants are growing, where the plant propagation materials of the useful plants are sown or where the plant propagation materials of the useful plants will be placed into the soil. An example for such a locus is a field, on which crop plants are growing.

The term "plant propagation material" is understood to denote generative parts of a plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds.

A further aspect of the instant invention is a method of protecting natural substances of plant and/or animal origin, which have been taken from the natural life cycle, and/or their processed forms against attack of fungi, which comprises applying to said natural substances of plant and/or animal origin or their processed forms a combination of components A) and B) in a synergistically effective amount.

According to the instant invention, the term "natural substances of plant origin, which have been taken from the natural life cycle" denotes plants or parts thereof which have been harvested from the natural life cycle and which are in the freshly harvested form. Examples of such natural substances of plant origin are stalks, leafs, tubers, seeds, fruits or grains. According to the instant invention, the term "processed form of a natural substance of plant origin" is understood to denote a form of a natural substance of plant origin that is the result of a modification process. Such modification processes can be used to transform the natural substance of plant origin in a more storable form of such a substance (a storage good). Examples of such modification processes are pre-drying, moistening, crushing, comminuting, grounding, compressing or roasting. Also falling under the definition of a processed form of a natural substance of plant origin is timber, whether in the form of crude timber, such as construction timber, electricity pylons and barriers, or in the form of finished articles, such as furniture or objects made from wood.

According to the instant invention, the term "natural substances of animal origin, which have been taken from the natural life cycle and/or their processed forms" is understood to denote material of animal origin such as skin, hides, leather, furs, hairs and the like.

The combinations according the present invention can prevent disadvantageous effects such as decay, discoloration or mold.

A preferred embodiment is a method of protecting natural substances of plant origin, which have been taken from the natural life cycle, and/or their processed forms against attack of fungi, which comprises applying to said natural substances of plant and/or animal origin or their processed forms a combination of components A) and B) in a synergistically effective amount.

A further preferred embodiment is a method of protecting fruits, preferably pomes, stone fruits, soft fruits and citrus fruits, which have been taken from the natural life cycle, and/or their processed forms, which comprises applying to said fruits and/or their processed forms a combination of components A) and B) in a synergistically effective amount.

The combinations of the present invention may also be used in the field of protecting industrial material against attack of fungi. According to the instant invention, the term "industrial material" denotes non-live material which have been prepared for use in industry. For example, industrial materials which are intended to be protected against attack of fungi can be glues, sizes, paper, board, textiles, carpets, leather, wood, constructions, paints, plastic articles, cooling lubricants, aqueous hydraulic fluids and other materials which can be infested with, or decomposed by, microorganisms. Cooling and heating systems, ventilation and air conditioning systems and parts of production plants, for example cooling-water circuits, which may be impaired by multiplication of microorganisms may also be mentioned from amongst the materials to be protected. The combinations according the present invention can prevent disadvantageous effects such as decay, discoloration or mold.

The combinations of the present invention may also be used in the field of protecting technical material against attack of fungi. According to the instant invention, the term "technical material" includes paper; carpets; constructions; cooling and heating systems; ventilation and air conditioning systems and the like. The combinations according the present invention can prevent disadvantageous effects such as decay, discoloration or mold.

The combinations according to the present invention are particularly effective against powdery mildews; rusts; leafspot species; early blights and molds; especially against *Septoria, Puccinia, Erysiphe, Pyrenophora* and *Tapesia* in cereals; *Phakopsora* in soybeans; *Hemileia* in coffee; *Phragmidium* in roses; *Alternaria* in potatoes, tomatoes and cucurbits; *Sclerotinia* in turf, vegetables, sunflower and oil seed rape; black rot, red fire, powdery mildew, grey mold and dead arm disease in vine; *Botrytis cinerea* in fruits; *Monilinia* spp. in fruits and *Penicillium* spp. in fruits.

The combinations according to the present invention are furthermore particularly effective against seedborne and soilborne diseases, such as *Alternaria* spp., *Ascochyta* spp., *Botrytis cinerea, Cercospora* spp., *Claviceps purpurea, Cochliobolus sativus, Colletotrichum* spp., *Epicoccum* spp., *Fusarium graminearum, Fusarium moniliforme, Fusarium oxysporum, Fusarium proliferatum, Fusarium solani, Fusarium subglutinans, Gaumannomyces graminis, Helminthosporium* spp., *Microdochium nivale, Phoma* spp., *Pyrenophora graminea, Pyricularia oryzae, Rhizoctonia solani, Rhizoctonia cerealis, Sclerotinia* spp., *Septoria* spp., *Sphacelotheca reilliana, Tilletia* spp., *Typhula incarnata, Urocystis occulta, Ustilago* spp. or *Verticillium* spp.; in particular against pathogens of cereals, such as wheat, barley, rye or oats; maize; rice; cotton; soybean; turf; sugarbeet; oil seed rape; potatoes; pulse crops, such as peas, lentils or chickpea; and sunflower.

The combinations according to the present invention are furthermore particularly effective against post harvest diseases such as *Botrytis cinerea, Colletotrichum musae, Curvularia lunata, Fusarium semitecum, Geotrichum candidum, Monilinia fructicola, Monilinia fructigena, Monilinia laxa, Mucor piriformis, Penicilium italicum, Penicilium solitum, Penicillium digitatum* or *Penicillium expansum* in particular against pathogens of fruits, such as pomefruits, for example apples and pears, stone fruits, for example peaches and plums, citrus, melons, papaya, kiwi, mango, berries, for example strawberries, avocados, pomegranates and bananas, and nuts.

The amount of a combination of the invention to be applied, will depend on various factors, such as the compounds employed; the subject of the treatment, such as, for example plants, soil or seeds; the type of treatment, such as, for example spraying, dusting or seed dressing; the purpose of the treatment, such as, for example prophylactic or therapeutic; the type of fungi to be controlled or the application time.

It has been found that the use of components B) in combination with the compound of formula I surprisingly and substantially enhance the effectiveness of the latter against fungi, and vice versa. Additionally, the method of the invention is effective against a wider spectrum of such fungi that can be combated with the active ingredients of this method, when used solely.

The weight ratio of A):B) is so selected as to give a synergistic activity. In general the weight ratio of A):B) is between 2000:1 and 1:1000, preferably between 100:1 and 1:100, more preferably between 20:1 and 1:50.

The synergistic activity of the combination is apparent from the fact that the fungicidal activity of the composition of A)+B) is greater than the sum of the fungicidal activities of A) and B).

The method of the invention comprises applying to the useful plants, the locus thereof or propagation material thereof in admixture or separately, a synergistically effective aggregate amount of a compound of formula I and a compound of component B).

Some of said combinations according to the invention have a systemic action and can be used as foliar, soil and seed treatment fungicides.

With the combinations according to the invention it is possible to inhibit or destroy the phytopathogenic microorganisms which occur in plants or in parts of plants (fruit, blossoms, leaves, stems, tubers, roots) in different useful plants, while at the same time the parts of plants which grow later are also protected from attack by phytopathogenic microorganisms.

The combinations of the present invention are of particular interest for controlling a large number of fungi in various useful plants or their seeds, especially in field crops such as potatoes, tobacco and sugarbeets, and wheat, rye, barley, oats, rice, maize, lawns, cotton, soybeans, oil seed rape, pulse crops, sunflower, coffee, sugarcane, fruit and ornamentals in horticulture and viticulture, in vegetables such as cucumbers, beans and cucurbits.

The combinations according to the invention are applied by treating the fungi, the useful plants, the locus thereof, the propagation material thereof, the natural substances of plant and/or animal origin, which have been taken from the natural life cycle, and/or their processed forms, or the industrial materials threatened by fungus attack with a combination of components A) and B) in a synergistically effective amount.

The combinations according to the invention may be applied before or after infection of the useful plants, the propagation material thereof, the natural substances of plant and/or animal origin, which have been taken from the natural life cycle, and/or their processed forms, or the industrial materials by the fungi.

The combinations according to the invention are particularly useful for controlling the following plant diseases: *Alternaria* species in fruit and vegetables, *Ascochyta* species in pulse crops, *Botrytis cinerea* in strawberries, tomatoes, sunflower, pulse crops, vegetables and grapes, *Cercospora arachidicola* in peanuts, *Cochliobolus sativus* in cereals, *Colletotrichum* species in pulse crops, *Erysiphe* species in cereals, *Erysiphe cichoracearum* and *Sphaerotheca fuliginea* in cucurbits, *Fusarium* species in cereals and maize, *Gaumannomyces graminis* in cereals and lawns, *Helminthosporium* species in maize, rice and potatoes, *Hemileia vastatrix* on coffee, *Microdochium* species in wheat and rye, *Phakopsora* species in soybean, *Puccinia* species in cereals, broadleaf crops and perennial plants, *Pseudocercosporella* species in cereals, *Phragmidium mucronatum* in roses, *Podosphaera* species in fruits, *Pyrenophora* species in barley, *Pyricularia oryzae* in rice, *Ramularia collo-cygni* in barley, *Rhizoctonia* species in cotton, soybean, cereals, maize, potatoes, rice and lawns, *Rhynchosporium secalis* in barley and rye, *Sclerotinia* species in lawns, lettuce, vegetables and oil seed rape, *Septoria* species in cereals, soybean and vegetables, *Sphacelotheca reilliana* in maize, *Tilletia* species in cereals, *Uncinula necator*, *Guignardia bidwellii* and *Phomopsis viticola* in vines, *Urocystis occulta* in rye, *Ustilago* species in cereals and maize, *Venturia* species in fruits, *Monilinia* species on fruits, *Penicillium* species on citrus and apples.

The combinations according to the invention are preventively and/or curatively valuable active ingredients in the field of pest control, even at low rates of application, which have a very favorable biocidal spectrum and are well tolerated by warm-blooded species, fish and plants. The active ingredients according to the invention which are partially known for their insecticidal action act against all or individual developmental stages of normally sensitive, but also resistant, animal pests, such as insects or representatives of the order Acarina. The insecticidal or acaricidal activity of the combinations according to the invention can manifest itself directly, i.e. in destruction of the pests, which takes place either immediately or only after some time has elapsed, for example during ecdysis, or indirectly, for example in a reduced oviposition and/or hatching rate, a good activity corresponding to a destruction rate (mortality) of at least 50 to 60%.

Examples of the abovementioned animal pests are:
from the order Acarina, for example,
*Acarus siro, Aceria sheldoni, Aculus schlechtendali, Amblyomma* spp., *Argas* spp., *Boophilus* spp., *Brevipalpus* spp., *Bryobia praetiosa, Calipitrimerus* spp., *Chorioptes* spp., *Dermanyssus gallinae, Eotetranychus carpini, Eriophyes* spp., *Hyalomma* spp., *Ixodes* spp., *Olygonychus pratensis*, *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Tarsonemus* spp. and *Tetranychus* spp.;
from the order Anoplura, for example,
*Haematopinus* spp., *Linognathus* spp., *Pediculus* spp., *Pemphigus* spp. and *Phylloxera* spp.;
from the order Coleoptera, for example,
*Agriotes* spp., *Anthonomus* spp., *Atomaria linearis, Chaetocnema tibialis, Cosmopolites* spp., *Curculio* spp., *Dermestes* spp., *Diabrotica* spp., *Epilachna* spp., *Eremnus* spp., *Leptinotarsa decemlineata, Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp., *Scarabeidae, Sitophilus* spp., *Sitotroga* spp., *Tenebrio* spp., *Tribolium* spp. and *Trogoderma* spp.;
from the order Diptera, for example,
*Aedes* spp., *Antherigona soccata, Bibio hortulanus, Calliphora erythrocephala, Ceratitis* spp., *Chrysomyia* spp., *Culex* spp., *Cuterebra* spp., *Dacus* spp., *Drosophila melanogaster, Fannia* spp., *Gastrophilus* spp., *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit, Pegomyia hyoscyami, Phorbia* spp., *Rhagoletis pomonella, Sciara* spp., *Stomoxys* spp., *Tabanus* spp., *Tannia* spp. and *Tipula* spp.;
from the order Heteroptera, for example,
*Cimex* spp., *Distantiella theobroma, Dysdercus* spp., *Euchistus* spp., *Eurygaster* spp., *Leptocorisa* spp., *Nezara* spp., *Piesma* spp., *Rhodnius* spp., *Sahlbergella singularis, Scotinophara* spp. and *Triatoma* spp.;
from the order Homoptera, for example,
*Aleurothrixus floccosus, Aleyrodes brassicae, Aonidiella* spp., *Aphididae, Aphis* spp., *Aspidiotus* spp., *Bemisia tabaci, Ceroplaster* spp., *Chrysomphalus aonidium, Chrysomphalus dictyospermi, Coccus hesperidum, Empoasca* spp., *Eriosoma larigerum, Erythroneura* spp., *Gascardia* spp., *Laodelphax* spp., *Lecanium corni, Lepidosaphes* spp., *Macrosiphus* spp., *Myzus* spp., *Nephotettix* spp., *Nilaparvata* spp., *Parlatoria* spp., *Pemphigus* spp., *Planococcus* spp., *Pseudaulacaspis* spp., *Pseudococcus* spp., *Psylla* spp., *Pulvinaria aethiopica, Quadraspidiotus* spp., *Rhopalosiphum* spp., *Saissetia* spp., *Scaphoideus* spp., *Schizaphis* spp., *Sitobion* spp., *Trialeurodes vaporariorum, Trioza erytreae* and *Unaspis citri*;
from the order Hymenoptera, for example,
*Acromyrmex, Atta* spp., *Cephus* spp., *Diprion* spp., *Diprionidae, Gilpinia polytoma, Hoplocampa* spp., *Lasius* spp., *Monomorium pharaonis, Neodiprion* spp., *Solenopsis* spp. and *Vespa* spp.;
from the order Isoptera, for example,
*Reticulitermes* spp.;
from the order Lepidoptera, for example,
*Acleris* spp., *Adoxophyes* spp., *Aegeria* spp., *Agrotis* spp., *Alabama argillaceae, Amylois* spp., *Anticarsia gemmatalis, Archips* spp., *Argyrotaenia* spp., *Autographa* spp., *Busseola fusca, Cadra cautella, Carposina nipponensis, Chilo* spp., *Choristoneura* spp., *Clysia ambiguella, Cnaphalocrocis* spp., *Cnephasia* spp., *Cochylis* spp., *Coleophora* spp., *Crocidolomia binotalis, Cryptophlebia leucotreta, Cydia* spp., *Diatraea* spp., *Diparopsis castanea, Earias* spp., *Ephestia* spp., *Eucosma* spp., *Eupoecilia ambiguella, Euproctis* spp., *Euxoa* spp., *Grapholita* spp., *Hedya nubiferana, Heliothis* spp., *Hellula undalis, Hyphantria cunea, Keiferia lycopersicella, Leucoptera scitella, Lithocollethis* spp., *Lobesia botrana, Lymantria* spp., *Lyonetia* spp., *Malacosoma* spp., *Mamestra brassicae, Manduca sexta, Operophtera* spp., *Ostrinia nubilalis, Pammene* spp., *Pandemis* spp., *Panolis flammea, Pectinophora gossypiela, Phthorimaea operculella, Pieris rapae, Pieris* spp., *Plutella xylostella, Prays* spp., *Scirpophaga* spp., *Sesamia* spp., *Sparganothis* spp., *Spodoptera* spp., *Synanthedon* spp., *Thaumetopoea* spp., *Tortrix* spp., *Trichoplusia ni* and *Yponomeuta* spp.;
from the order Mallophaga, for example,
*Damalinea* spp. and *Trichodectes* spp.;
from the order Orthoptera, for example,
*Blatta* spp., *Blattella* spp., *Gryllotalpa* spp., *Leucophaea maderae, Locusta* spp., *Periplaneta* spp. and *Schistocerca* spp.;
from the order Psocoptera, for example,
*Liposcelis* spp.;
from the order Siphonaptera, for example,
*Ceratophyllus* spp., *Ctenocephalides* spp. and *Xenopsylla cheopis*;
from the order Thysanoptera, for example,
*Frankliniella* spp., *Hercinothrips* spp., *Scirtothrips aurantii, Taeniothrips* spp., *Thrips palmi* and *Thrips tabaci*;
from the order Thysanura, for example,
*Lepisma saccharina*;
nematodes, for example root knot nematodes, stem eelworms and foliar nematodes; especially *Heterodera* spp., for example *Heterodera schachtii, Heterodora avenae* and *Het-*

*erodora trifolii; Globodera* spp., for example *Globodera rostochiensis; Meloidogyne* spp., for example *Meloidogyne incoginita* and *Meloidogyne javanica; Radopholus* spp., for example *Radopholus similis; Pratylenchus*, for example *Pratylenchus neglectans* and *Pratylenchus penetrans; Tylenchulus*, for example *Tylenchulus semipenetrans; Longidorus, Trichodorus, Xiphinema, Ditylenchus, Aphelenchoides* and *Anguina;* crucifer flea beetles (*Phyllotreta* spp.);

root maggots (*Delia* spp.) and cabbage seedpod weevil (*Ceutorhynchus* spp.).

The combinations according to the invention can be used for controlling, i.e. containing or destroying, animal pests of the abovementioned type which occur on useful plants in agriculture, in horticulture and in forests, or on organs of useful plants, such as fruits, flowers, foliage, stalks, tubers or roots, and in some cases even on organs of useful plants which are formed at a later point in time remain protected against these animal pests.

When applied to the useful plants the compound of formula I is applied at a rate of 5 to 2000 g a.i./ha, particularly 10 to 1000 g a.i./ha, e.g. 50, 75, 100 or 200 g a.i./ha, in association with 1 to 5000 g a.i./ha, particularly 2 to 2000 g a.i./ha, e.g. 100, 250, 500, 800, 1000, 1500 g a.i./ha of a compound of component B), depending on the class of chemical employed as component B).

In agricultural practice the application rates of the combination according to the invention depend on the type of effect desired, and typically range from 20 to 4000 g of total combination per hectare.

When the combinations of the present invention are used for treating seed, rates of 0.001 to 50 g of a compound of formula I per kg of seed, preferably from 0.01 to 10 g per kg of seed, and 0.001 to 50 g of a compound of component B), per kg of seed, preferably from 0.01 to 10 g per kg of seed, are generally sufficient.

The invention also provides fungicidal compositions comprising a compound of formula I and a compound of component B) in a synergistically effective amount.

The composition of the invention may be employed in any conventional form, for example in the form of a twin pack, a powder for dry seed treatment (DS), an emulsion for seed treatment (ES), a flowable concentrate for seed treatment (FS), a solution for seed treatment (LS), a water dispersible powder for seed treatment (WS), a capsule suspension for seed treatment (CF), a gel for seed treatment (GF), an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP) or any technically feasible formulation in combination with agriculturally acceptable adjuvants.

Such compositions may be produced in conventional manner, e.g. by mixing the active ingredients with appropriate formulation inerts (diluents, solvents, fillers and optionally other formulating ingredients such as surfactants, biocides, anti-freeze, stickers, thickeners and compounds that provide adjuvancy effects). Also conventional slow release formulations may be employed where long lasting efficacy is intended. Particularly formulations to be applied in spraying forms, such as water dispersible concentrates (e.g. EC, SC, DC, OD, SE, EW, EO and the like), wettable powders and granules, may contain surfactants such as wetting and dispersing agents and other compounds that provide adjuvancy effects, e.g. the condensation product of formaldehyde with naphthalene sulphonate, an alkylarylsulphonate, a lignin sulphonate, a fatty alkyl sulphate, and ethoxylated alkylphenol and an ethoxylated fatty alcohol.

A seed dressing formulation is applied in a manner known per se to the seeds employing the combination of the invention and a diluent in suitable seed dressing formulation form, e.g. as an aqueous suspension or in a dry powder form having good adherence to the seeds. Such seed dressing formulations are known in the art. Seed dressing formulations may contain the single active ingredients or the combination of active ingredients in encapsulated form, e.g. as slow release capsules or microcapsules.

In general, the formulations include from 0.01 to 90% by weight of active agent, from 0 to 20% agriculturally acceptable surfactant and 10 to 99.99% solid or liquid formulation inerts and adjuvant(s), the active agent consisting of at least the compound of formula I together with a compound of component B), and optionally other active agents, particularly microbiocides or conservatives or the like. Concentrated forms of compositions generally contain in between about 2 and 80%, preferably between about 5 and 70% by weight of active agent. Application forms of formulation may for example contain from 0.01 to 20% by weight, preferably from 0.01 to 5% by weight of active agent. Whereas commercial products will preferably be formulated as concentrates, the end user will normally employ diluted formulations.

The Examples which follow serve to illustrate the invention, "active ingredient" denoting a mixture of compound I and a compound of component B) in a specific mixing ratio.

FORMULATION EXAMPLES

| Wettable powders | a) | b) | c) |
|---|---|---|---|
| active ingredient [I:comp B) = 1:3(a), 1:2(b), 1:1(c)] | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The active ingredient is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredient [I:comp B) = 1:3(a), 1:2(b), 1:1(c)] | 25% | 50% | 75% |
| light mineral oil | 5% | 5% | 5% |
| highly dispersed silicic acid | 5% | 5% | — |
| Kaolin | 65% | 40% | — |
| Talcum | — | — | 20 |

The active ingredient is thoroughly mixed with the adjuvants and the mixture is thoroughly ground in a suitable mill, affording powders that can be used directly for seed treatment.

| Emulsifiable concentrate | |
|---|---|
| active ingredient (I:comp B) = 1:6) | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredient [I:comp B = 1:6(a), 1:2(b), 1:10(c)] | 5% | 6% | 4% |
| talcum | 95% | — | — |
| Kaolin | — | 94% | — |
| mineral filler | — | — | 96% |

Ready-for-use dusts are obtained by mixing the active ingredient with the carrier and grinding the mixture in a suitable mill. Such powders can also be used for dry dressings for seed.

| Extruder granules | |
|---|---|
| Active ingredient (I:comp B) = 2:1) | 15% |
| sodium lignosulfonate | 2% |
| carboxymethylcellulose | 1% |
| Kaolin | 82% |

The active ingredient is mixed and ground with the adjuvants, and the mixture is moistened with water. The mixture is extruded and then dried in a stream of air.

| Coated granules | |
|---|---|
| Active ingredient (I:comp B) = 1:10) | 8% |
| polyethylene glycol (mol. wt. 200) | 3% |
| Kaolin | 89% |

The finely ground active ingredient is uniformly applied, in a mixer, to the kaolin moistened with polyethylene glycol. Non-dusty coated granules are obtained in this manner.

| Suspension concentrate | |
|---|---|
| active ingredient (I:comp B) = 1:8) | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

| Flowable concentrate for seed treatment | |
|---|---|
| active ingredient (I:comp B) = 1:8) | 40% |
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of a combination of the compound of formula I and a compound of component B), or of each of these compounds separately, are mixed with 2 parts of an aromatic solvent and 7 parts of toluene diisocyanate/polymethylene-polyphenyl-isocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed.

The obtained capsule suspension is stabilized by adding 0.25 parts of a thickener and 3 parts of a dispersing agent. The capsule suspension formulation contains 28% of the active ingredients.

The medium capsule diameter is 8-15 microns.

The resulting formulation is applied to seeds as an aqueous suspension in an apparatus suitable for that purpose.

BIOLOGICAL EXAMPLES

A synergistic effect exists whenever the action of an active ingredient combination is greater than the sum of the actions of the individual components.

The action to be expected E for a given active ingredient combination obeys the so-called COLBY formula and can be calculated as follows (COLBY, S. R. "Calculating synergistic and antagonistic responses of herbicide combination". Weeds, Vol. 15, pages 20-22; 1967):

ppm=milligrams of active ingredient (=a.i.) per liter of spray mixture

X=% action by active ingredient A) using p ppm of active ingredient

Y=% action by active ingredient B) using q ppm of active ingredient.

According to COLBY, the expected (additive) action of active ingredients A)+B) using p+q ppm of active ingredient is $$E = X + Y - \frac{X \cdot Y}{100}$$

If the action actually observed (O) is greater than the expected action (E), then the action of the combination is super-additive, i.e. there is a synergistic effect. In mathematical terms the synergism factor SF corresponds to O/E. In the agricultural practice an SF of ≧1.2 indicates significant improvement over the purely complementary addition of activities (expected activity), while an SF of ≦0.9 in the practical application routine signals a loss of activity compared to the expected activity.

EXAMPLE B-1

Action Against *Botrytis cinerea* on Grapes a) Fungal Growth Assay

Conidia of the fungus from cryogenic storage were directly mixed into nutrient broth (PDB potato dextrose broth). After placing a (DMSO) solution of the test compounds into a microtiter plate (96-well format) the nutrient broth containing the fungal spores was added. The test plates were incubated at 24° C. and the inhibition of growth was determined photometrically after 48-72 hrs. The fungicide interactions in the combinations are calculated according to COLBY method.

Control of *Botrytis cinerea*
Dosage in mg active ingredient/liter final medium

| Cpd Ic in ppm [mg/L] | Azoxystrobin in ppm [mg/L] | Expected control in % (% $C_{exp}$) expected | Observed control in % (% $C_{obs}$) observed | Synergy Factor SF = % $C_{obs}$/% $C_{exp}$ Factor |
|---|---|---|---|---|
| 0.0222 | — | — | 23 | — |
| 0.0074 | — | — | 10 | — |
| 0.0025 | — | — | 0 | — |
| — | 1.80 | — | 14 | — |
| — | 0.60 | — | 7 | — |
| 0.0222 | 1.80 | 34 | 54 | 1.6 |
| 0.0074 | 1.80 | 22 | 34 | 1.5 |
| 0.0025 | 1.80 | 14 | 27 | 1.9 |
| 0.0222 | 0.60 | 28 | 43 | 1.5 |
| 0.0074 | 0.60 | 16 | 31 | 1.9 |
| 0.0025 | 0.60 | 7 | 16 | 2.2 |

| Cpd Ic in ppm [mg/L] | Prothioconazole in ppm [mg/L] | Expected control in % (% $C_{exp}$) expected | Observed control in % (% $C_{obs}$) observed | Synergy Factor SF = % $C_{obs}$/% $C_{exp}$ Factor |
|---|---|---|---|---|
| — | 0.2000 | — | 52 | — |
| — | 0.0667 | — | 17 | — |
| — | 0.0222 | — | 8 | — |
| 0.0667 | — | — | 35 | — |
| 0.0222 | — | — | 18 | — |
| 0.0222 | 0.2000 | 60 | 94 | 1.5 |

| Cpd Ic in ppm [mg/L] | Picoxystrobin in ppm [mg/L] | Expected control in % (% $C_{exp}$) expected | Observed control in % (% $C_{obs}$) observed | Synergy Factor SF = % $C_{obs}$/% $C_{exp}$ Factor |
|---|---|---|---|---|
| — | 0.6000 | — | 20 | — |
| — | 0.2000 | — | 12 | — |
| — | 0.0667 | — | 6 | — |
| — | 0.0222 | — | 0 | — |
| 0.2000 | — | — | 71 | — |
| 0.0667 | — | — | 28 | — |
| 0.0222 | — | — | 12 | — |
| 0.0222 | 0.6000 | 29 | 88 | 3.0 |
| 0.0222 | 0.2000 | 22 | 88 | 4.0 |
| 0.0222 | 0.0667 | 17 | 85 | 4.9 |

In comparative examples B-1 to B-8 as component A) a specific compound of formula Ic was used. Said compound of formula Ic was a compound of formula Ic, which represents an epimeric mixture of the racemic compounds of formula Ia (syn) and Ib (anti), wherein the ratio of the racemic compound of formula Ia (syn), which represents a racemic mixture of the single enantiomers of formulae $I_{III}$ and $I_{IV}$, to the racemic compound of formula Ib (anti), which represents a racemic mixture of the single enantiomers of formula $I_V$ and $I_{VI}$, was 9:1.

b) Protective Treatment 5 week old grape seedlings cv. Gutedel are treated with the formulated test compound (0.02% active ingredient) in a spray chamber. Two days after application, the grape plants are inoculated by spraying a spore suspension (1×10⁶ conidia/ml) on the test plants. After an incubation period of 4 days at 21° C. and 95% relative humidity in a greenhouse the disease incidence is assessed. The fungicide interactions in the combinations are calculated according to COLBY method.

EXAMPLE B-2

Action Against *Septoria tritici* on Wheat a) Fungal Growth Assay

Conidia of the fungus from cryogenic storage were directly mixed into nutrient broth (PDB potato dextrose broth). After placing a (DMSO) solution of the test compounds into a microtiter plate (96-well format) the nutrient broth containing the fungal spores was added. The test plates were incubated at 24° C. and the inhibition of growth was determined photometrically after 72 hrs. The fungicide interactions in the combinations are calculated according to COLBY method.

Control of *Septoria tritici*

| Cpd Ic in ppm [mg/L] | Propiconazole in ppm [mg/L] | Expected control in % (% $C_{exp}$) expected | Observed control in % (% $C_{obs}$) observed | Synergy Factor SF = % $C_{obs}$/% $C_{exp}$ Factor |
|---|---|---|---|---|
| 0.0008 | — | — | 13 | — |
| 0.0001 | — | — | 1 | — |
| — | 0.067 | — | 7 | — |
| — | 0.007 | — | 0 | — |
| 0.0008 | 0.067 | 19 | 34 | 1.8 |
| 0.0001 | 0.007 | 1 | 8 | 6.4 | b) Protective Treatment 2 week old wheat plants cv. Riband are treated with the formulated test compound (0.2% active ingredient) in a spray chamber. One day after application, wheat plants are inoculated by spraying a spore suspension (10×10⁵ conidia/ml) on the test plants. After an incubation period of 1 day at 23° C. and 95% relative humidity, the plants are kept for 16 days at 23° C. and 60% relative humidity in a greenhouse. The disease incidence is assessed 18 days after inoculation. The fungicide interactions in the combinations are calculated according to COLBY method.

EXAMPLE B-3

Action Against *Pyricularia oryzae* on Rice a) Fungal Growth Assay

Conidia of the fungus from cryogenic storage were directly mixed into nutrient broth (PDB potato dextrose broth). After placing a (DMSO) solution of the test compounds into a microtiter plate (96-well format) the nutrient broth containing the fungal spores was added. The test plates were incubated at 24° C. and the inhibition of growth was determined photometrically after 72 hrs. The fungicide interactions in the combinations are calculated according to COLBY method.

| Cpd Ic in ppm [mg/L] | Cyprodinil in ppm [mg/L] | Expected control in % (% $C_{exp}$) expected | Observed control in % (% $C_{obs}$) observed | Synergy Factor SF = % $C_{obs}$/% $C_{exp}$ Factor |
|---|---|---|---|---|
| Control of *Pyricularia oryzae* Dosage in mg active ingredient/liter final medium | | | | |
| 0.0222 | — | — | 59 | — |
| 0.0074 | — | — | 33 | — |
| 0.0025 | — | — | 13 | — |
| — | 0.067 | — | 0 | — |
| — | 0.007 | — | 0 | — |
| — | 0.002 | — | 0 | — |
| 0.0074 | 0.067 | 33 | 42 | 1.3 |
| 0.0074 | 0.007 | 33 | 40 | 1.2 |
| 0.0074 | 0.002 | 33 | 41 | 1.3 |

| Cpd Ic in ppm [mg/L] | Chlorothalonil in ppm [mg/L] | Expected control in % (% $C_{exp}$) expected | Observed control in % (% $C_{obs}$) observed | Synergy Factor SF = % $C_{obs}$/% $C_{exp}$ Factor |
|---|---|---|---|---|
| Control of *Pyricularia oryzae* Dosage in mg active ingredient/liter final medium | | | | |
| 0.0222 | — | — | 59 | — |
| 0.0074 | — | — | 33 | — |
| 0.0025 | — | — | 13 | — |
| — | 0.067 | — | 0 | — |
| — | 0.007 | — | 0 | — |
| — | 0.002 | — | 0 | — |
| 0.0074 | 0.067 | 33 | 42 | 1.3 |
| 0.0074 | 0.007 | 33 | 40 | 1.2 |
| 0.0074 | 0.002 | 33 | 41 | 1.3 |

| Cpd Ic in ppm [mg/L] | Cyproconazole in ppm [mg/L] | Expected control in % (% $C_{exp}$) expected | Observed control in % (% $C_{obs}$) observed | Synergy Factor SF = % $C_{obs}$/% $C_{exp}$ Factor |
|---|---|---|---|---|
| Control of *Pyricularia oryzae* | | | | |
| 0.0025 | — | — | 6 | — |
| 0.0008 | — | — | 3 | — |
| 0.0001 | — | — | 2 | — |
| — | 0.200 | — | 0 | — |
| — | 0.022 | — | 0 | — |
| 0.0025 | 0.200 | 6 | 11 | 1.8 |
| 0.0008 | 0.200 | 3 | 9 | 3.2 |
| 0.0001 | 0.200 | 2 | 4 | 2.0 |
| 0.0025 | 0.022 | 6 | 16 | 2.7 |
| 0.0008 | 0.022 | 3 | 5 | 1.7 |
| 0.0001 | 0.022 | 2 | 3 | 1.2 | b) Protective Treatment

Rice leaf segments are placed on agar in multiwell plates (24-well format) and sprayed with test solutions. After drying, the leaf disks are inoculated with a spore suspension of the fungus. After appropriate incubation the activity of a compound is assessed 96 hrs after inoculation as preventive fungicidal activity. The fungicide interactions in the combinations are calculated according to COLBY method.

EXAMPLE B-4

Action Against *Alternaria solani* (Early Blight)

a) Fungal Growth Assay

Conidia—harvested from a freshly grown colony—of the fungus were directly mixed into nutrient broth (PDB potato dextrose broth). After placing a (DMSO) solution of the test compounds into a microtiter plate (96-well format) the nutrient broth containing the fungal spores was added. The test plates were incubated at 24° C. and the inhibition of growth was determined photometrically after 48 hrs. The fungicide interactions in the combinations are calculated according to COLBY method.

| Cpd Ic in ppm [mg/L] | Fludioxonil in ppm [mg/L] | Expected control in % (% $C_{exp}$) expected | Observed control in % (% $C_{obs}$) observed | Synergy Factor SF = % $C_{obs}$/% $C_{exp}$ Factor |
|---|---|---|---|---|
| Control of *Alternaria solani* Dosage in mg active ingredient/liter final medium | | | | |
| 0.0074 | — | — | 27 | — |
| 0.0025 | — | — | 8 | — |
| — | 0.067 | — | 24 | — |
| — | 0.022 | — | 1 | — |
| 0.0074 | 0.067 | 44 | 62 | 1.4 |
| 0.0025 | 0.067 | 30 | 45 | 1.5 |
| 0.0074 | 0.022 | 27 | 37 | 1.3 |
| 0.0025 | 0.022 | 9 | 11 | 1.3 | b) Protective Treatment 4 week old tomato plants cv. Roter Gnom are treated with the formulated test compound (0.02% active ingredient) in a spray chamber. Two days after application, the tomato plants are inoculated by spraying a spore suspension ($2 \times 10^5$ conidia/ml) on the test plants. After an incubation period of 3 days at 20° C. and 95% relative humidity in a growth chamber the disease incidence is assessed. The fungicide interactions in the combinations are calculated according to COLBY method.

EXAMPLE B-5

Action Against *Pyrenophora teres* (Net Blotch)

a) Fungal Growth Assay

Conidia of the fungus from cryogenic storage were directly mixed into nutrient broth (PDB potato dextrose broth). After placing a (DMSO) solution of the test compounds into a microtiter plate (96-well format) the nutrient broth containing the fungal spores was added. The test plates were incubated at 24° C. and the inhibition of growth was determined photometrically after 48 hrs. The fungicide interactions in the combinations are calculated according to COLBY method.

| Cpd Ic in ppm [mg/L] | Cpd F-1 in ppm [mg/L] | Expected control in % (% $C_{exp}$) expected | Observed control in % (% $C_{obs}$) observed | Synergy Factor SF = % $C_{obs}$/% $C_{exp}$ Factor |
|---|---|---|---|---|
| Control of *Pyrenophora teres* | | | | |
| — | 16.2 | — | 6 | — |
| — | 5.4 | — | 2 | — |
| 0.2000 | — | — | 55 | — |

Control of *Pyrenophora teres* (continued)

| Cpd Ic in ppm [mg/L] | Cpd F-1 in ppm [mg/L] | Expected control in % (% $C_{exp}$) expected | Observed control in % (% $C_{obs}$) observed | Synergy Factor SF = % $C_{obs}$/% $C_{exp}$ Factor |
|---|---|---|---|---|
| 0.0667 | — | — | 37 | — |
| 0.2000 | 16.2 | 58 | 73 | 1.3 |
| 0.2000 | 5.4 | 56 | 72 | 1.3 |
| 0.0667 | 16.2 | 41 | 56 | 1.4 |
| 0.0667 | 5.4 | 38 | 57 | 1.5 | b) Protective Treatment

Barley leaf segments are placed on agar in multiwell plates (24-well format) and sprayed with test solutions. After drying, the leaf disks are inoculated with a spore suspension of the fungus. After appropriate incubation the activity of a compound is assessed 96 hrs after inoculation as preventive fungicidal activity. The fungicide interactions in the combinations are calculated according to COLBY method.

EXAMPLE B-6

Action Against *Venturia inaequalis* on Apple a) Fungal Growth Assay

Conidia of the fungus from cryogenic storage were directly mixed into nutrient broth (PDB potato dextrose broth). After placing a (DMSO) solution of the test compounds into a microtiter plate (96-well format) the nutrient broth containing the fungal spores was added. The test plates were incubated at 24° C. and the inhibition of growth was determined photometrically after 144 hrs. The fungicide interactions in the combinations are calculated according to COLBY method.

Control of *Venturia inaequalis*

| Cpd Ic in ppm [mg/L] | Cpd B-1 in ppm [mg/L] | Expected control in % (% $C_{exp}$) expected | Observed control in % (% $C_{obs}$) observed | Synergy Factor SF = % $C_{obs}$/% $C_{exp}$ Factor |
|---|---|---|---|---|
| — | 0.0074 | — | 61 | — |
| — | 0.0025 | — | 32 | — |
| — | 0.0008 | — | 17 | — |
| 0.2000 | — | — | 59 | — |
| 0.0667 | — | — | 18 | — |
| 0.0222 | — | — | 6 | — |
| 0.0667 | 0.0025 | 44 | 55 | 1.2 |
| 0.0667 | 0.0008 | 32 | 57 | 1.8 |

| Cpd Ic in ppm [mg/L] | Fenpropimorph in ppm [mg/L] | Expected control in % (% $C_{exp}$) expected | Observed control in % (% $C_{obs}$) observed | Synergy Factor SF = % $C_{obs}$/% $C_{exp}$ Factor |
|---|---|---|---|---|
| — | 0.0222 | — | 33 | — |
| — | 0.0025 | — | 0 | — |
| 0.0667 | — | — | 18 | — |
| 0.0222 | — | — | 10 | — |
| 0.0222 | 0.0222 | 39 | 53 | 1.3 |
| 0.0222 | 0.0025 | 10 | 33 | 3.4 | b) Protective Treatment 4 week old apple seedlings cv. McIntosh are treated with the formulated test compound (0.02% active ingredient) in a spray chamber. One day after application, the apple plants are inoculated by spraying a spore suspension (4×10⁵ conidia/ml) on the test plants. After an incubation period of 4 days at 21° C. and 95% relative humidity the plants are placed for 4 days at 21° C. and 60% relative humidity in a greenhouse. After another 4 day incubation period at 21° C. and 95% relative humidity the disease incidence is assessed. The fungicide interactions in the combinations are calculated according to COLBY method.

EXAMPLE B-7

Action Against *Pythium ultimum* (Damping Off)—Fungal Growth Assay

Mycelial fragments of the fungus, prepared from a fresh liquid culture, were directly mixed into nutrient broth (PDB potato dextrose broth). After placing a (DMSO) solution of the test compounds into a microtiter plate (96-well format) the nutrient broth containing the fungal spores was added. The test plates were incubated at 24° C. and the inhibition of growth was determined photometrically after 48 hrs. The fungicide interactions in the combinations are calculated according to COLBY method.

Control of *Pythium ultimum*

| Cpd Ic in ppm [mg/L] | Fenpropidin in ppm [mg/L] | Expected control in % (% $C_{exp}$) expected | Observed control in % (% $C_{obs}$) observed | Synergy Factor SF = % $C_{obs}$/% $C_{exp}$ Factor |
|---|---|---|---|---|
| — | 16.2000 | — | 34 | — |
| — | 5.4000 | — | 11 | — |
| 0.6000 | — | — | 0 | — |
| 0.2000 | — | — | 0 | — |
| 0.0667 | — | — | 0 | — |
| 0.2000 | 16.2000 | 34 | 48 | 1.4 |

EXAMPLE B-8

Action Against *Leptosphaeria nodorum* (Glume Blotch)—Fungal Growth Assay

Conidia of the fungus from cryogenic storage were directly mixed into nutrient broth (PDB potato dextrose broth). After placing a (DMSO) solution of the test compounds into a microtiter plate (96-well format) the nutrient broth containing the fungal spores was added. The test plates were incubated at 24° C. and the inhibition of growth was determined photometrically after 48 hrs. The fungicide interactions in the combinations are calculated according to COLBY method.

Control of *Leptosphaeria nodorum*

| Cpd Ic in ppm [mg/L] | Epoxiconazole in ppm [mg/L] | Expected control in % (% $C_{exp}$) expected | Observed control in % (% $C_{obs}$) observed | Synergy Factor SF = % $C_{obs}$/% $C_{exp}$ Factor |
|---|---|---|---|---|
| — | 0.0222 | — | 39 | — |
| — | 0.0025 | — | 9 | — |
| 0.0667 | — | — | 0 | — |
| 0.0222 | — | — | 0 | — |
| 0.0222 | 0.0222 | 39 | 91 | 2.3 |
| 0.0222 | 0.0025 | 9 | 21 | 2.3 |

-continued

| | | Control of *Leptosphaeria nodorum* | | |
|---|---|---|---|---|
| Cpd Ic in ppm [mg/L] | Difenoconazole in ppm [mg/L] | Expected control in % (% $C_{exp}$) expected | Observed control in % (% $C_{obs}$) observed | Synergy Factor SF = % $C_{obs}$/% $C_{exp}$ Factor |
| — | 0.0074 | — | 73 | — |
| — | 0.0025 | — | 16 | — |
| — | 0.0008 | — | 5 | — |
| 0.2000 | — | — | 0 | — |
| 0.0667 | — | — | 0 | — |
| 0.2000 | 0.0025 | 16 | 88 | 5.5 |
| 0.2000 | 0.0008 | 5 | 74 | 13.8 |
| 0.0667 | 0.0025 | 16 | 21 | 1.3 |
| 0.0667 | 0.0008 | 5 | 10 | 1.8 |

EXAMPLE B-9

Action Against *Pseudocercosporella herpotrichoides* var. *acuformis* (Eyespot/Cereals)—Fungal Growth Assay Conidia of the fungus from cryogenic storage were directly mixed into nutrient broth (PDB potato dextrose broth). After placing a (DMSO) solution of the test compounds into a microtiter plate (96-well format) the nutrient broth containing the fungal spores was added. The test plates were incubated at 24° C. and the inhibition of growth was determined photometrically after 72 hrs. The fungicide interactions in the combinations are calculated according to COLBY method.

EXAMPLE B-10

Action Against *Ustilago maydis* (Corn Smut)—Fungal Growth Assay

Conidia of the fungus from cryogenic storage were directly mixed into nutrient broth (PDB potato dextrose broth). After placing a (DMSO) solution of the test compounds into a microtiter plate (96-well format) the nutrient broth containing the fungal spores was added. The test plates were incubated at 24° C. and the inhibition of growth was determined photometrically after 48 hrs. The fungicide interactions in the combinations are calculated according to COLBY method.

EXAMPLE B-11

Action Against *Phytophthora infestans* (Late Blight) on Tomato—Protective Treatment Tomato leaf disks are placed on water agar in multiwell plates (24-well format) and sprayed with test solutions. After drying, the leaf disks are inoculated with a spore suspension of the fungus. After appropriate incubation the activity of a compound is assessed 96 hrs after inoculation as preventive fungicidal activity. The fungicide interactions in the combinations are calculated according to COLBY method.

EXAMPLE B-12

Action Against *Plasmopara viticola* (Downy Mildew) on Grape Vines—Protective Treatment Grape vine leaf disks are placed on agar in multiwell plates (24-well format) and sprayed with test solutions. After drying, the leaf disks are inoculated with a spore suspension of the fungus. After appropriate incubation the activity of a compound is assessed 7 days after inoculation as preventive fungicidal activity. The fungicide interactions in the combinations are calculated according to COLBY method.

EXAMPLE B-13

Action Against *Botrytis cinerea* (Grey Mould) on Beans—Protective Treatment

Bean leaf disks are placed on agar in multiwell plates (24-well format) and sprayed with test solutions. After drying, the leaf disks are inoculated with a spore suspension of the fungus. After appropriate incubation the activity of a compound is assessed 96 hrs after inoculation as preventive fungicidal activity. The fungicide interactions in the combinations are calculated according to COLBY method.

EXAMPLE B-14

Action Against *Erysiphe graminis* f.sp. *hordei* (Barley Powdery Mildew) on Barley—Protective Treatment Barley leaf segments are placed on agar in multiwell plates (24-well format) and sprayed with test solutions. After drying, the leaf disks are inoculated with a spore suspension of the fungus. After appropriate incubation the activity of a compound is assessed 96 hrs after inoculation as preventive fungicidal activity. The fungicide interactions in the combinations are calculated according to COLBY method.

EXAMPLE B-15

Action Against *Erysiphe graminis* f.sp. *tritici* (Wheat Powdery Mildew) on Barley—Protective Treatment Barley leaf segments are placed on agar in multiwell plates (24-well format) and sprayed with test solutions. After drying, the leaf disks are inoculated with a spore suspension of the fungus. After appropriate incubation the activity of a compound is assessed 96 hrs after inoculation as preventive fungicidal activity. The fungicide interactions in the combinations are calculated according to COLBY method.

EXAMPLE B-16

Action Against *Puccinia recondita* (Brown Rust) on Wheat a) Protective Treatment of Leaf Segments
Wheat leaf segments are placed on agar in multiwell plates (24-well format) and sprayed with test solutions. After drying, the leaf disks are inoculated with a spore suspension of the fungus. After appropriate incubation the activity of a compound is assessed 9 days after inoculation as preventive fungicidal activity. The fungicide interactions in the combinations are calculated according to COLBY method.

b) Protective Treatment of Plants
1 week old wheat plants cv. Arina are treated with the formulated test compound (0.02% active ingredient) in a spray chamber. One day after application, the wheat plants are inoculated by spraying a spore suspension ($1\times10^5$ uredospores/ml) on the test plants. After an incubation period of 2 days at 20° C. and 95% relative humidity the plants are kept in a greenhouse for 8 days at 20° C. and 60% relative humidity. The disease incidence is assessed 10 days after inoculation. The fungicide interactions in the combinations are calculated according to COLBY method.

EXAMPLE B-17

Action Against *Septoria nodorum* on Wheat a) Protective Treatment of Leaf Segments Wheat leaf segments are placed on agar in multiwell plates (24-well format) and sprayed with test solutions. After drying, the leaf disks are inoculated with a spore suspension of the fungus. After appropriate incubation the activity of a compound is assessed 96 hrs after inoculation as preventive fungicidal activity. The fungicide interactions in the combinations are calculated according to COLBY method.

b) Protective Treatment of Plants 1 week old wheat plants cv. Arina are treated with the formulated test compound (0.02% active ingredient) in a spray chamber. One day after application, the wheat plants are inoculated by spraying a spore suspension ($5 \times 10^5$ conidia/ml) on the test plants. After an incubation period of 1 day at 20° C. and 95% relative humidity the plants are kept for 10 days at 20° C. and 60% relative humidity in a greenhouse. The disease incidence is assessed 11 days after inoculation. The fungicide interactions in the combinations are calculated according to COLBY method.

EXAMPLE B-18

Action Against *Podosphaera leucotricha* (Powdery Mildew) on Apple—Protective Treatment 5 week old apple seedlings cv. McIntosh are treated with the formulated test compound (0.02% active ingredient) in a spray chamber. One day after, the application apple plants are inoculated by shaking plants infected with apple powdery mildew above the test plants. After an incubation period of 12 days at 22° C. and 60% relative humidity under a light regime of 14/10 hours (light/dark) the disease incidence is assessed. The fungicide interactions in the combinations are calculated according to COLBY method.

EXAMPLE B-19

Action Against *Erysiphe graminis* (Powdery Mildew) on Barley—Protective Treatment 1 week old barley plants cv. Regina are treated with the formulated test compound (0.02% active ingredient) in a spray chamber. One day after application, the barley plants are inoculated by shaking powdery mildew infected plants above the test plants. After an incubation period of 6 days at 20° C./18° C. (day/night) and 60% relative humidity in a greenhouse the disease incidence is assessed. The fungicide interactions in the combinations are calculated according to COLBY method.

EXAMPLE B-20

Action Against *Botrytis cinerea* on Tomatoes—Protective Treatment 4 week old tomato plants cv. Roter Gnom are treated with the formulated test compound (0.02% active ingredient) in a spray chamber. Two days after application, the tomato plants are inoculated by spraying a spore suspension ($1 \times 10^5$ conidia/ml) on the test plants. After an incubation period of 4 days at 20° C. and 95% relative humidity in a growth chamber the disease incidence is assessed. The fungicide interactions in the combinations are calculated according to COLBY method.

EXAMPLE B-21

Action Against *Helminthosporium teres* (Net Blotch) on Barley—Protective Treatment 1 week old barley plants cv. Regina are treated with the formulated test compound (0.02% active ingredient) in a spray chamber. Two days after application, the barley plants are inoculated by spraying a spore suspension ($3 \times 10^4$ conidia/ml) on the test plants. After an incubation period of 4 days at 20° C. and 95% relative humidity in a greenhouse the disease incidence is assessed. The fungicide interactions in the combinations are calculated according to COLBY method.

EXAMPLE B-22

Action Against *Uncinula necator* (Powdery Mildew) on Grapes—Protective Treatment 5 week old grape seedlings cv. Gutedel are treated with the formulated test compound (0.02% active ingredient) in a spray chamber. One day after application, the grape plants are inoculated by shaking plants infected with grape powdery mildew above the test plants. After an incubation period of 7 days at 26° C. and 60% relative humidity under a light regime of 14/10 hours (light/dark) the disease incidence is assessed. The fungicide interactions in the combinations are calculated according to COLBY method.

The combinations according to the invention exhibit good activity in all of the above examples.

What is claimed is:

1. A method of controlling phytopathogenic diseases on useful plants or on propagation material thereof, which comprises applying to the useful plants, the locus thereof or propagation material thereof a combination of components A) and B) in a synergistically effective amount, wherein component A) is a compound of formula I

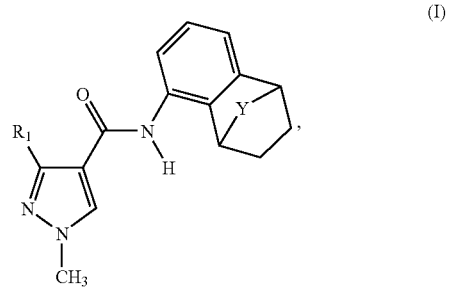

(I)

wherein $R_1$ is difluoromethyl, Y is —$CHR_2$—, and $R_2$ is isopropyl; or a tautomer of such a compound; and component B) is a compound selected from the group consisting of a triazole fungicide; prochloraz; a compound of formula B-1

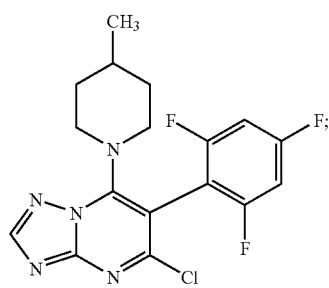

chlorothalonil; fluazinam; dithianon; metrafenone; tricyclazole; mefenoxam; acibenzolar-S-methyl; and a compound of formula A10

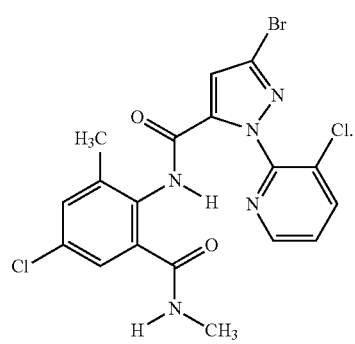

2. A method according to claim 1, wherein component A) is a compound of formula Ic

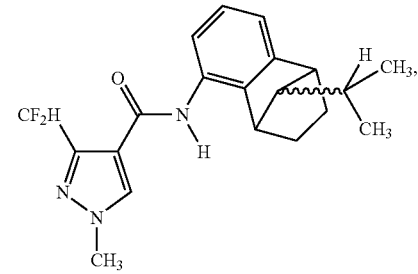

which represents an epimeric mixture of racemic compounds of formula Ia (syn)

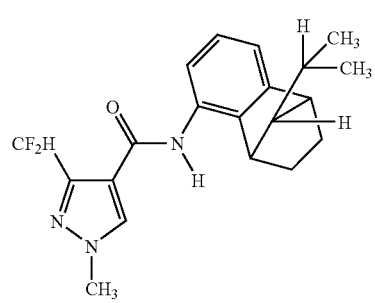

and racemic compounds of formula Ib (anti)

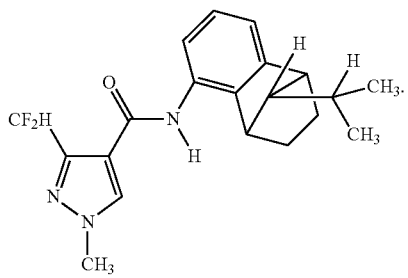

3. A method according to claim 2, wherein the racemic compound of formula Ia (syn) is present in an amount of from 80 to 99% by weight.

4. A method according to claim 1, wherein compound B) is a compound of formula B-1.

5. A method of protecting natural substances of plant or animal origin, which have been taken from the natural life cycle, or their processed forms, which comprises applying to the natural substances of plant or animal origin or their processed forms a combination of components A) and B) in a synergistically effective amount, wherein component A) is a compound of formula I

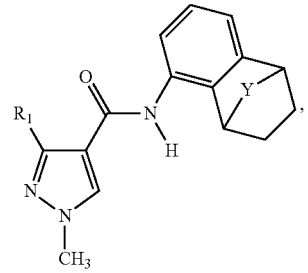

wherein $R_1$ is difluoromethyl, Y is —$CHR_2$—, and $R_7$ is isopropyl; or a tautomer of such a compound; and component B) is a compound selected from the group consisting of a triazole fungicide; prochloraz; a compound of formula B-1

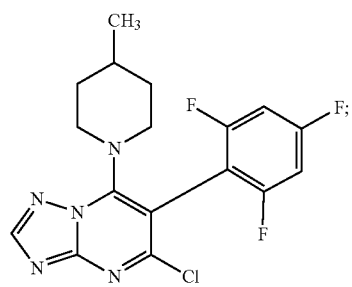

chlorothalonil; fluazinam; dithianon; metrafenone; tricyclazole; mefenoxam; acibenzolar-S-methyl; and a compound of formula A10

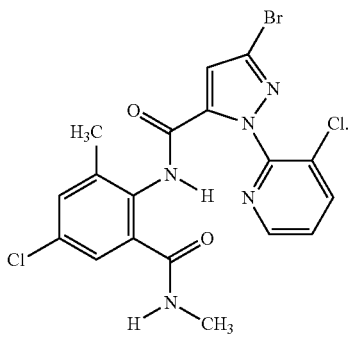

(A-10)

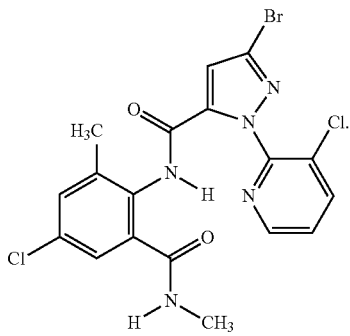

(A-10)

6. A fungicidal composition comprising a combination of components A) and B) in a synergistically effective amount, together with an agriculturally acceptable carrier, and optionally a surfactant, wherein component A) is a compound of formula I

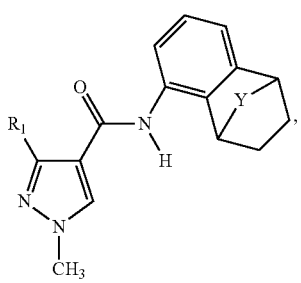

(I)

wherein $R_1$ is difluoromethyl, Y is —$CHR_2$—, and $R_2$ is isopropyl; or a tautomer of such a compound; and component B) is a compound selected from the group consisting of a triazole fungicide; prochloraz; a compound of formula B-1

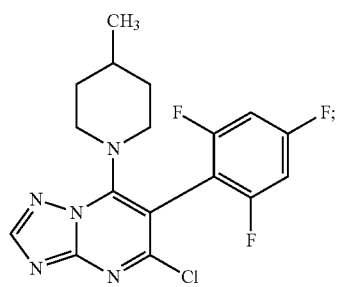

(B-1)

chlorothalonil; fluazinam; dithianon; metrafenone; tricyclazole; mefenoxam; acibenzolar-S-methyl; and a compound of formula A10

7. A fungicidal composition according to claim 6, wherein compound B) is a triazole fungicide selected from the group consisting of azaconazole, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, penconazole, propiconazole, prothioconazole, simeconazole, tebuconazole, tetraconazole, triadimefon, triadimenol, tricyclazole, triticonazole, diclobutrazol, etaconazole, furconazole, furconazole-cis and quinconazole.

8. A fungicidal composition according to claim 7, wherein compound B) is a triazole fungicide selected from the group consisting of ipconazole, metconazole, penconazole, tebuconazole and tricyclazole.

9. A fungicidal composition according to claim 6, wherein compound B) is a compound of formula B-1.

10. A method according to claim 5, wherein compound B) is a compound of formula B-1.

11. A method according to claim 5, wherein compound B) is a triazole fungicide selected from the group consisting of azaconazole, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, penconazole, propiconazole, prothioconazole, simeconazole, tebuconazole, tetraconazole, triadimefon, triadimenol, tricyclazole, triticonazole, diclobutrazol, etaconazole, furconazole, furconazole-cis and quinconazole.

12. A method according to claim 11, wherein compound B) is a triazole fungicide selected from the group consisting of ipconazole, metconazole, penconazole, tebuconazole and tricyclazole.

13. A method according to claim 1, wherein compound B) is a triazole triazole fungicide selected from the group consisting of azaconazole, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, penconazole, propiconazole, prothioconazole, simeconazole, tebuconazole, tetraconazole, triadimefon, triadimenol, tricyclazole, triticonazole, diclobutrazol, etaconazole, furconazole, furconazole-cis and quinconazole.

14. A method according to claim 13, wherein compound B) is a triazole fungicide selected from the group consisting of ipconazole, metconazole, penconazole, tebuconazole and tricyclazole.

* * * * *